US012751743B2

(12) United States Patent
Dewey et al.

(10) Patent No.: US 12,751,743 B2
(45) Date of Patent: Oct. 6, 2026

(54) SPINAL IMPLANT SYSTEM AND METHOD

(71) Applicant: Warsaw Orthopedic, Inc., Warsaw, IN (US)

(72) Inventors: Jonathan M. Dewey, Memphis, TN (US); Shane Lars Riding, Bartlett, TN (US); Julien J. Prevost, Memphis, TN (US); William Alan Rezach, Covington, TN (US); Jeffrey Warren Beale, Bartlett, TN (US); Gregory Thomas Poulter, Zionsville, IN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 702 days.

(21) Appl. No.: 18/076,766

(22) Filed: Dec. 7, 2022

(65) Prior Publication Data

US 2024/0188992 A1 Jun. 13, 2024

(51) Int. Cl.
*A61B 17/70* (2006.01)
*A61B 17/58* (2006.01)
*A61B 17/86* (2006.01)

(52) U.S. Cl.
CPC .......... *A61B 17/7037* (2013.01); *A61B 17/58* (2013.01); *A61B 17/7035* (2013.01); *A61B 17/86* (2013.01)

(58) Field of Classification Search
CPC ........................ A61B 17/7035; A61B 17/7037
See application file for complete search history.

(56) References Cited

U.S. PATENT DOCUMENTS

| | | | | |
|---|---|---|---|---|
| 5,207,678 | A | 5/1993 | Harms et al. | |
| 5,443,467 | A * | 8/1995 | Biedermann | A61B 17/7037 606/328 |
| 5,575,792 | A | 11/1996 | Errico et al. | |
| 5,609,593 | A | 3/1997 | Errico et al. | |
| 5,609,654 | A | 3/1997 | Le et al. | |
| 5,630,817 | A | 5/1997 | Rokegem et al. | |
| 5,643,263 | A | 7/1997 | Simonson | |
| 5,797,911 | A | 8/1998 | Sherman et al. | |

(Continued)

FOREIGN PATENT DOCUMENTS

| | | |
|---|---|---|
| CN | 101594832 | 12/2009 |
| CN | 102596067 | 7/2012 |

(Continued)

OTHER PUBLICATIONS

Coric et al., "Percutaneous, Navigated Minimally Invasive Posterior Cervical Pedicle Screw Fixation," International Journal of Spine Surgery, vol. 14, Suppl. 3, Dec. 9, 2020, pp. S14-S21.

(Continued)

*Primary Examiner* — Larry E Waggle, Jr.
(74) *Attorney, Agent, or Firm* — Sheridan Ross P.C.

(57) ABSTRACT

A spinal implant includes a first member defining an implant cavity. A second member is movable relative to the first member and penetrable with tissue. A first crown is engageable with the first member, and a second crown is engageable with the second member. The second crown being movable relative to the first crown to fix the first member relative to the second member in a selected orientation. In some embodiments, systems, spinal constructs and methods are disclosed.

11 Claims, 17 Drawing Sheets

(56) References Cited

U.S. PATENT DOCUMENTS

| | | | | |
|---|---|---|---|---|
| 5,885,285 | A | 3/1999 | Simonson | |
| 5,885,286 | A * | 3/1999 | Sherman | A61B 17/7037 606/270 |
| 5,947,967 | A | 9/1999 | Barker | |
| 6,074,391 | A | 6/2000 | Metz-Stavenhagen et al. | |
| 6,226,548 | B1 | 5/2001 | Foley et al. | |
| 6,280,442 | B1 | 8/2001 | Barker et al. | |
| 6,520,962 | B1 | 2/2003 | Taylor et al. | |
| 6,562,038 | B1 | 5/2003 | Morrison | |
| 6,572,618 | B1 | 6/2003 | Morrison | |
| 6,579,292 | B2 | 6/2003 | Taylor | |
| 6,648,887 | B2 | 11/2003 | Ashman | |
| 6,685,705 | B1 | 2/2004 | Taylor | |
| 6,755,830 | B2 | 6/2004 | Minfelde et al. | |
| 6,872,209 | B2 | 3/2005 | Morrison | |
| 7,066,939 | B2 | 6/2006 | Taylor | |
| 7,867,255 | B2 | 1/2011 | Miller et al. | |
| 7,927,360 | B2 | 4/2011 | Pond, Jr. et al. | |
| 7,976,567 | B2 | 7/2011 | Null et al. | |
| 8,277,489 | B2 | 10/2012 | Saidha et al. | |
| 8,298,275 | B2 | 10/2012 | Rezach | |
| 8,419,773 | B2 | 4/2013 | Biedermann et al. | |
| 8,430,913 | B2 | 4/2013 | James et al. | |
| 8,523,911 | B2 | 9/2013 | Jani et al. | |
| 8,535,352 | B2 * | 9/2013 | Altarac | A61B 17/7014 606/267 |
| 8,574,274 | B2 * | 11/2013 | Courtney | A61B 17/7034 606/279 |
| 8,585,741 | B2 | 11/2013 | Gabelberger et al. | |
| 8,672,978 | B2 | 3/2014 | Dant et al. | |
| 8,795,337 | B2 | 8/2014 | Wilcox et al. | |
| 8,992,575 | B1 | 3/2015 | Di Lauro et al. | |
| 9,155,580 | B2 | 10/2015 | Cormier et al. | |
| 9,247,964 | B1 | 2/2016 | Shoshtaev | |
| 9,314,274 | B2 | 4/2016 | Amstutz et al. | |
| 9,387,013 | B1 | 7/2016 | Shoshtaev et al. | |
| 9,402,663 | B2 | 8/2016 | Peterson et al. | |
| 9,629,663 | B2 | 4/2017 | Ludwig et al. | |
| 10,130,395 | B2 * | 11/2018 | Leff | A61B 17/7037 |
| 10,238,432 | B2 | 3/2019 | Carruth et al. | |
| 10,335,201 | B2 | 7/2019 | Rezach | |
| 10,413,331 | B2 | 9/2019 | Gregory | |
| 10,736,665 | B2 | 8/2020 | Bobbitt et al. | |
| 10,835,291 | B2 | 11/2020 | May | |
| 10,966,760 | B2 | 4/2021 | Armstrong et al. | |
| 11,147,593 | B2 * | 10/2021 | Biedermann | A61B 17/7032 |
| 11,234,738 | B2 * | 2/2022 | Jackson | A61B 17/7035 |
| 11,291,477 | B1 | 4/2022 | Rezach et al. | |
| 11,890,033 | B1 | 2/2024 | McBride et al. | |
| 2002/0029040 | A1 | 3/2002 | Morrison et al. | |
| 2004/0162558 | A1 | 8/2004 | Hegde et al. | |
| 2005/0049588 | A1 | 3/2005 | Jackson | |
| 2005/0197660 | A1 | 9/2005 | Haid, Jr. et al. | |
| 2005/0228326 | A1 | 10/2005 | Kalfas et al. | |
| 2005/0240180 | A1 | 10/2005 | Vienney et al. | |
| 2005/0273101 | A1 | 12/2005 | Schumacher | |
| 2006/0058794 | A1 | 3/2006 | Jackson | |
| 2006/0083603 | A1 | 4/2006 | Jackson | |
| 2007/0055244 | A1 | 3/2007 | Jackson | |
| 2007/0191840 | A1 | 8/2007 | Pond, Jr. et al. | |
| 2008/0015584 | A1 | 1/2008 | Richelsoph | |
| 2008/0177323 | A1 | 7/2008 | Null et al. | |
| 2008/0183215 | A1 | 7/2008 | Altarac et al. | |
| 2008/0262553 | A1 | 10/2008 | Hawkins et al. | |
| 2008/0294194 | A1 | 11/2008 | Capote et al. | |
| 2010/0087864 | A1 | 4/2010 | Klein et al. | |
| 2010/0087867 | A1 | 4/2010 | Klein et al. | |
| 2010/0094345 | A1 | 4/2010 | Saidha et al. | |
| 2010/0160981 | A1 | 6/2010 | Butler et al. | |
| 2010/0318131 | A1 | 12/2010 | James et al. | |
| 2010/0324599 | A1 | 12/2010 | Montello et al. | |
| 2011/0257690 | A1 | 10/2011 | Rezach | |
| 2012/0046701 | A1 | 2/2012 | Gennari et al. | |
| 2012/0109208 | A1 | 5/2012 | Justis et al. | |
| 2012/0130436 | A1 | 5/2012 | Haskins et al. | |
| 2014/0214084 | A1 | 7/2014 | Jackson et al. | |
| 2015/0351809 | A1 | 12/2015 | Jackson et al. | |
| 2016/0166289 | A1 | 6/2016 | Alsup et al. | |
| 2017/0348026 | A1 | 12/2017 | Stein et al. | |
| 2018/0206890 | A1 | 7/2018 | Rezach | |
| 2018/0228516 | A1 | 8/2018 | Armstrong et al. | |
| 2018/0228518 | A1 | 8/2018 | Carruth et al. | |
| 2018/0243009 | A1 | 8/2018 | Bobbitt et al. | |
| 2019/0029729 | A1 | 1/2019 | Mire et al. | |
| 2019/0150990 | A1 | 5/2019 | Jackson et al. | |
| 2020/0146724 | A1 | 5/2020 | Italiaie | |
| 2020/0268452 | A1 | 8/2020 | Rezach et al. | |
| 2020/0405395 | A1 | 12/2020 | Gullotti et al. | |
| 2021/0145519 | A1 | 5/2021 | Mosnier et al. | |
| 2021/0153904 | A1 | 5/2021 | Armstrong et al. | |
| 2021/0169531 | A1 | 6/2021 | Leff et al. | |
| 2021/0220018 | A1 | 7/2021 | Armstrong et al. | |
| 2024/0138881 | A1 | 5/2024 | Armstrong et al. | |

FOREIGN PATENT DOCUMENTS

| | | |
|---|---|---|
| CN | 202932996 | 3/2013 |
| CN | 103025255 | 4/2013 |
| CN | 103153219 | 6/2013 |
| DE | 202011107821 | 2/2012 |
| DE | 102011111403 | 10/2012 |
| EP | 3579770 | 12/2019 |
| FR | 2859620 | 3/2005 |
| WO | WO 2014/138614 | 9/2014 |
| WO | WO 2015/184012 | 12/2015 |

OTHER PUBLICATIONS

Coric et al., "Percutaneous Posterior Cervical Pedicle Instrumentation (C1 to C7) With Navigation Guidance: Early Series of 27 Cases," Global Spine Journal, vol. 12, No. 2S, pp. 27S-33S, 2022.

International Search Report and Written Opinion for International (PCT) Patent Application No. PCT/IB2023/062256, dated Mar. 20, 2024, 16 pages.

International Search Report and Written Opinion for International (PCT) Patent Application No. PCT/IB2023/060616, dated Jan. 29, 2024, 13 pages.

Official Action for China Patent Application No. 201810132125.8, dated Jan. 10, 2022, 22 pages.

Article 94(3) Communication for Europe Patent Application No. 18152721.9, dated Jun. 18, 2021, 7 pages.

Article 94(3) Communication for Europe Patent Application No. 18152721.9, dated Mar. 15, 2023, 4 pages.

Official Action for U.S. Appl. No. 17/976,163, dated Jun. 26, 2023, 12 pages.

Notice of Allowance for U.S. Appl. No. 17/976,163, dated Oct. 2, 2023, 5 pages.

Official Action for U.S. Appl. No. 15/337,229, dated May 11, 2017, 12 pages.

Official Action for U.S. Appl. No. 15/337,229, dated Dec. 14, 2017, 12 pages.

Official Action for U.S. Appl. No. 15/337,229, dated Apr. 3, 2018, 13 pages.

Official Action for U.S. Appl. No. 15/337,229, dated Oct. 19, 2018, 18 pages.

Official Action for U.S. Appl. No. 15/337,229, dated Apr. 3, 2019, 19 pages.

Official Action for U.S. Appl. No. 15/337,229, dated Oct. 11, 2019, 7 pages.

Official Action for U.S. Appl. No. 15/337,229, dated Feb. 7, 2020, 21 pages.

Notice of Allowance for U.S. Appl. No. 15/337,229, dated Dec. 11, 2020, 5 pages.

Official Action for U.S. Appl. No. 15/432,704, dated Aug. 1, 2018, 6 pages. Restriction Requirement.

Official Action for U.S. Appl. No. 15/432,704, dated Oct. 15, 2024, 10 pages.

Official Action for U.S. Appl. No. 15/432,704, dated Apr. 22, 2019, 23 pages.

(56) References Cited

OTHER PUBLICATIONS

Official Action for U.S. Appl. No. 15/432,704, dated Oct. 30, 2019, 25 pages.
Official Action for U.S. Appl. No. 15/432,704, dated Feb. 4, 2020, 26 pages.
Official Action for U.S. Appl. No. 15/432,704, dated May 13, 2020, 21 pages.
Official Action for U.S. Appl. No. 15/432,704, dated Sep. 18, 2020, 21 pages.
Official Action for U.S. Appl. No. 15/432,704, dated Feb. 24, 2021, 30 pages.
Official Action for U.S. Appl. No. 15/432,704, dated Jul. 28, 2021, 27 pages.
Official Action for U.S. Appl. No. 15/432,704, dated Oct. 28, 2021, 32 pages.
Official Action for U.S. Appl. No. 15/432,704, dated Dec. 17, 2021, 29 pages.
Official Action for U.S. Appl. No. 17/163,896, dated Nov. 23, 2022, 28 pages.
Official Action for U.S. Appl. No. 17/163,896, dated May 12, 2023, 29 pages.
Official Action for U.S. Appl. No. 17/163,896, dated Aug. 24, 2023, 32 pages.
Official Action for U.S. Appl. No. 17/163,896, dated Dec. 27, 2023, 31 pages.
Official Action for U.S. Appl. No. 17/163,896, dated May 28, 2024, 42 pages.
Official Action for U.S. Appl. No. 17/163,896, dated Oct. 18, 2024, 45 pages.
Official Action for U.S. Appl. No. 18/403,112, dated Jul. 22, 2025, 9 pages.

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a spinal implant is provided. The spinal implant includes a first member defining an implant cavity. A second member is movable relative to the first member and penetrable with tissue. A first crown is engageable with the first member. A second crown is engageable with the second member. The second crown is movable relative to the first crown to fix the first member relative to the second member in a selected orientation. In some embodiments, systems, spinal constructs and methods are disclosed.

In one embodiment, the spinal implant includes a receiver defining an implant cavity and one or more grooves. A shaft is movable relative to the receiver. One or more bands are configured for disposal within the one or more grooves and is engageable with a head of the shaft to connect the receiver and the shaft such that the receiver is movable relative to the shaft. A first crown is engageable with the receiver. A second crown is engageable with the shaft and movable relative to the first crown between a non locking orientation such that the receiver and the shaft include multi axial relative movement and a locking orientation such that the receiver is fixed relative to the shaft in a selected orientation.

In one embodiment, the spinal implant includes a first member defining an implant cavity and one or more grooves. A second member is configured to penetrate tissue. One or more bands are configured for disposal within the one or more grooves and is engageable with a head of the second member to connect the members such that the first member is movable relative to the second member. A crown is engageable with the members to fix the first member relative to the second member in a selected orientation. The crown includes a break away surface.

BRIEF DESCRIPTION OF THE DRAWINGS

The present disclosure will become more readily apparent from the specific description accompanied by the following drawings, in which.

DETAILED DESCRIPTION

Figure 1:
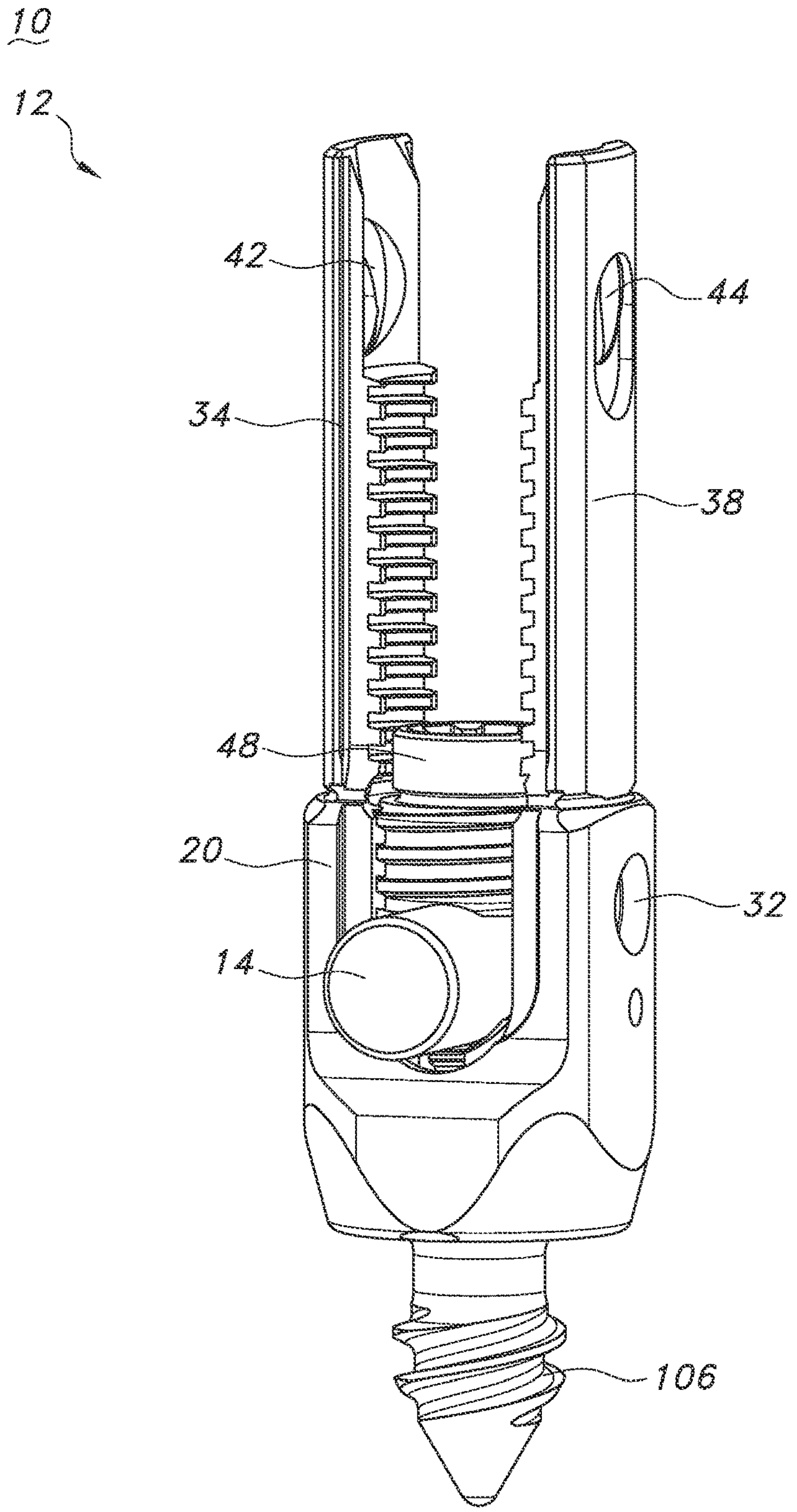
FIG. 1 is a perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the present surgical system includes a spinal implant, for example, a multi-axial bone fastener that is fixed with vertebral tissue and includes an implant receiver that is movable to receive a spinal implant, for example, a spinal rod. In some embodiments, the implant receiver is movable to a selected orientation for alignment and disposal of the spinal rod. In some embodiments, the bone fastener includes a first crown and a second crown configured to fix the implant receiver in the selected orientation. In some embodiments, the bone fastener includes a crown having a break away surface and being engageable with the implant receiver and a shaft configured to fix the implant receiver in the selected orientation. In some embodiments, the systems and methods of the present disclosure include surgical instruments and implants that are employed with a surgical treatment, as described herein, for example, with a cervical, thoracic, lumbar and/or sacral region of a spine.

In some embodiments, the present surgical system includes a spinal implant including a bone fastener, for example, a multi-axial bone screw. In some embodiments, the multi-axial bone screw is movable to a selected orientation relative to vertebral tissue and fixable in the selected orientation. In some embodiments, this configuration converts a multi-axial screw to a fixed angle screw. In some embodiments, the bone fastener includes an implant receiver, for example, a head and a dual crown assembly. In some embodiments, the head includes extender tabs and a dual ring configuration for a modular pop-on or snap fit assembly. In some embodiments, the crown assembly includes an outer crown and an inner crown. In some embodiments, the head includes a detent configured for engagement with the crown assembly. In some embodiments, the crown assembly is configured for disposal with the head. In some embodiments, the head is positioned above a ball of a shank of the bone fastener. In some embodiments, the head is translated in a downward direction onto the shank. In some embodiments, the crown assembly is translated in a downward direction past the detent in the head to lock the head to the shank.

In some embodiments, the present surgical system includes a spinal implant including a bone fastener movable between a pivoting position/non locked orientation and a fixed axial screw position/locked orientation. In some embodiments, in the pivoting position/non locked orientation, a socket disposed on an underside of an inner crown facilitates selectively pivoting of the head around a ball of the shank. In some embodiments, in the fixed axial screw position/locked orientation, the inner crown is threaded within the outer crown, and the socket of the inner crown engages a surface of the shank to prevent movement of the head around the ball of the shank. In some embodiments, the outer crown is driven against a head detent to create an opposing force of the threaded inner crown. In some embodiments, in the fixed axial screw position/locked orientation, a spinal rod is fixed with the head. In some embodiments, after spinal correction has been completed and the rod has been inserted into the head, the rod is fixed to the bone fastener via a setscrew. In some embodiments, the setscrew engages with the head and the rod, and is tightened.

In some embodiments, the present surgical system includes a bone fastener configured for disposal in a multi axial locked orientation. In some embodiments, this configuration maintains maneuverability and the ability of the head to pivot, for example, during rod insertion. In some embodiments, the multi axial orientation can be locked after the rod is inserted into the head and the set screw is tightened. In some embodiments, the set screw drives down on the rod, driving the socket of the inner crown onto the surface of the shank to prevent pivoting of the head. In some embodiments, the ability of the head to pivot is maintained during rod insertion such that there is provided a variability in the head positioning and/or ease of rod disposal.

In some embodiments, the present surgical system includes a bone fastener, for example, a multi-axial bone screw configured to be pivoted and fixed in a selected orientation to convert a multi-axial screw into a fixed angle screw. In some embodiments, a head of the bone screw is configured to pivot to accommodate a spinal rod. In some embodiments, when the bone fastener is fixed with a selected vertebra, the bone fastener can manipulate the vertebra using a head of the bone fastener as the head is locked in a fixed angle orientation. In some embodiments, the head is locked to the rod as a set screw is tightened. In some embodiments, the present surgical system includes a single bone fastener having multi-axial screw movement and fixed axial screw movement in a single spinal implant.

In some embodiments, the present surgical system includes a multi-axial screw having a dual crown assembly that includes an inner crown and an outer crown. In some embodiments, the inner crown includes an outer surface on a top of the inner crown that defines raised ridges. In some embodiments, the raised ridges are configured to increase an amount of thread for engaging the outer crown and are configured for increasing engagement of a surgical tool, for example, a driver with the inner crown. In some embodiments, the raised ridges increase an amount of thread for engaging the outer crown and compress so as to not interfere with set screw tightening to fix the rod with the head. In some embodiments, the inner crown includes a surface disposed on an underside or socket of the inner crown that defines deformable ribs. In some embodiments, the deformable ribs are configured to provide slip resistance when the inner socket of the crown engages with a ball of a shaft of the bone fastener.

In some embodiments, the present surgical system includes a bone fastener configured for use in a minimally invasive surgical technique. In some embodiments, the bone fastener includes a fixed-multi axial screw. In some embodiments, the bone fastener includes a threaded crown including a break off driving section. In some embodiments, the bone fastener is disposable in a selected orientation with selective angulation of a head of the bone fastener. In some embodiments, a set screw portion of the crown is removed via a break away portion to fix the head in the selected orientation. In some embodiments, a spinal rod is translated through the selectively aligned and fixed head. In some embodiments, the rod is fixed with the head. In some embodiments, the crown is configured to fix or lock the orientation of the head in a selected orientation. In some embodiments, the bone fastener provides de-rotation of vertebral tissue without fully locking the rod.

In some embodiments, the present bone fastener includes a fixed-multi axial screw. In some embodiments, the bone fastener is modular and a head is configured for pop-on or snap-fit engagement with a selected shaft of the bone fastener. In some embodiments, the bone fastener includes a threaded break off crown that is configured for alignment with an axis of the bone fastener to allow for use in a percutaneous workflow. In some embodiments, a spinal rod is configured to be seated in a rod slot or implant receiving surface that is formed in the head such that the broken off crown does not support the rod. In some embodiments, a selected amount of torque is applied to the bone fastener to fix the crown and remove the break off portion from the crown. In some embodiments, a user implements the break off crown to fix the head in a selected orientation.

In some embodiments, the present surgical system includes a bone fastener including a modular fixed-multi axial screw. In some embodiments, the modular fixed-multi axial screw includes a head movable to a selected orientation and lockable in the selected orientation using a crown including a break off portion. In some embodiments, in the selected orientation the crown is tightened in a downward direction using a break off driver and the break-off portion of the crown is removed. In some embodiments, the break off portion fixes the screw in the selected oriented, for example, a selected angle in a fixed angle screw configuration. In some embodiments, the modular fixed-multi axial screw provides alignment of one or more bone fastener heads before translating the rod through the heads and maintains the heads in the selected orientation. In some embodiments, the modular fixed-multi axial screw facilitates de-rotation maneuvers before the rod is fixed with the bone fasteners. In some embodiments, the bone fastener includes a multi-fixed axial screw.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal implant, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-21, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, for example, a bone fastener, at a surgical site of a patient, which includes, for example, a spine. In some embodiments, the spinal implant can include one or more components of one or more spinal constructs, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 2:
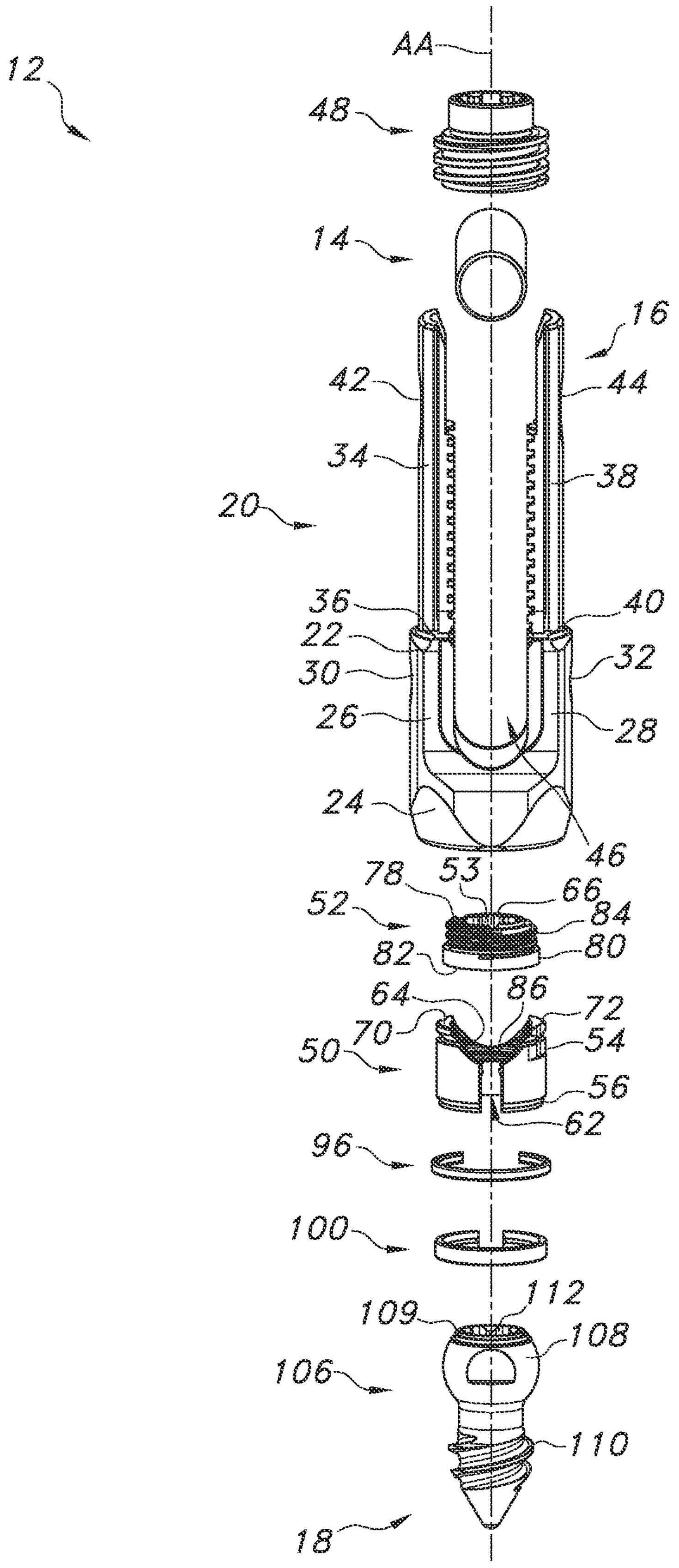
FIG. 2 is a perspective view of components shown in FIG. 1 with parts separated.

Spinal implant system 10 includes a spinal implant, for example, a bone fastener 12, as shown in FIGS. 1-2. Bone fastener 12 is configured for fixation with a surgical site including vertebral tissue via a member, for example, a shaft 106. Bone fastener 12 includes a member, for example, a receiver 20 configured to receive a spinal implant, for example, a spinal rod 14. Receiver 20 is movable to a selected orientation relative to vertebral tissue and fixable in the selected orientation, as described herein. In some embodiments, bone fastener 12 includes a multi-axial bone screw such that receiver 20 is movable to a selected orientation relative to vertebral tissue and fixable in the selected orientation. In some embodiments receiver 20 is movable between a pivoting position/non locked orientation and a fixed axial screw position/locked orientation with shaft 106 and/or vertebral tissue. Bone fastener 12 extends between an end 16, an end 18 and defines a longitudinal axis AA.

Receiver 20 is movable relative to shaft 106. Receiver 20 extends between a proximal end 22 and a distal end 24. End 22 includes an arm 26 and an arm 28. In some embodiments, arms 26, 28 each extend substantially parallel to axis AA. Arms 26, 28 each include an arcuate outer surface extending between a pair of side surfaces. In some embodiments, at least one of the outer surfaces and the side surfaces of arms 26, 28 have at least one recess or cavity 30, 32 therein, configured to receive an insertion tool, compression instrument and/or instruments for inserting and tensioning bone fastener 12.

Arm 26 is configured for connection with an extension 34 via a break away surface 36, and arm 28 is configured for connection with an extension 38 via a break away surface 40. Break away surfaces 36, 40 are configured to fracture and separate at a predetermined force or torque limit. Extensions 34, 38 each include an arcuate outer surface extending between a pair of side surfaces. In some embodiments, at least one of the outer surfaces and the side surfaces of extensions 34, 38 have at least one recess or cavity 42, 44 therein, configured to receive an insertion tool, compression instrument and/or instruments for inserting and tensioning bone fastener 12. In some embodiments, extensions 34, 38 include extender tabs.

Receiver 20 defines an implant cavity 46. Implant cavity 46 is configured for disposal of rod 14 and a setscrew 48, described herein. In some embodiments, cavity 46 may have various cross section configurations, for example, oval, oblong, triangular, rectangular, square, polygonal, irregular, uniform, non-uniform, variable and/or tapered.

Figure 9:
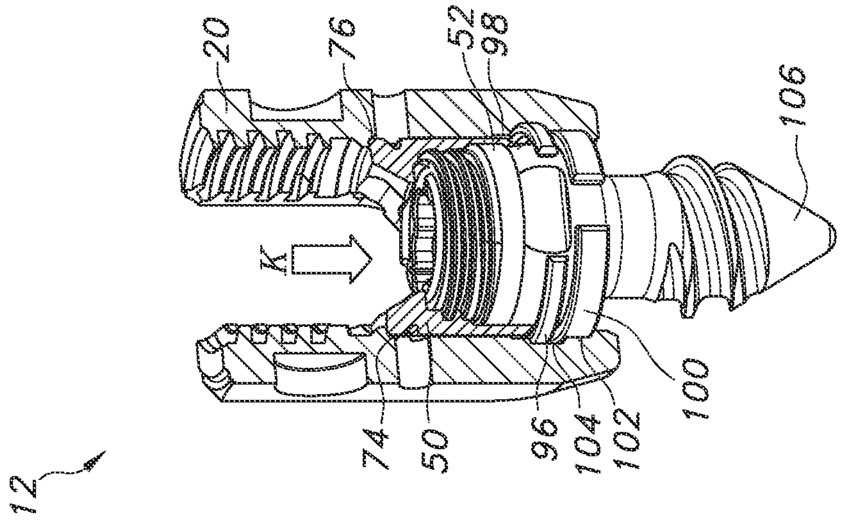
FIG. 9 is a perspective view in part cross section of the components of the system shown in FIG. 7.
Figure 8:
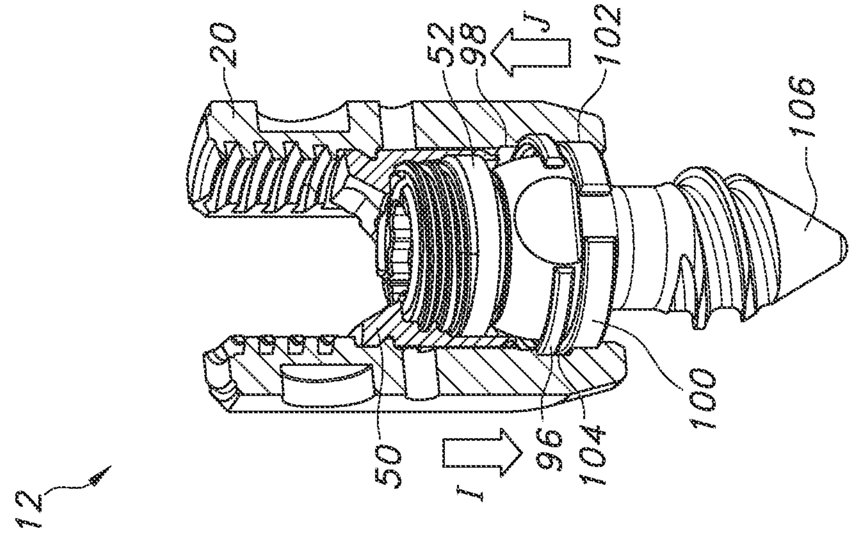
FIG. 8 is a perspective view in part cross section of the components of the system shown in FIG. 7.
Figure 7:
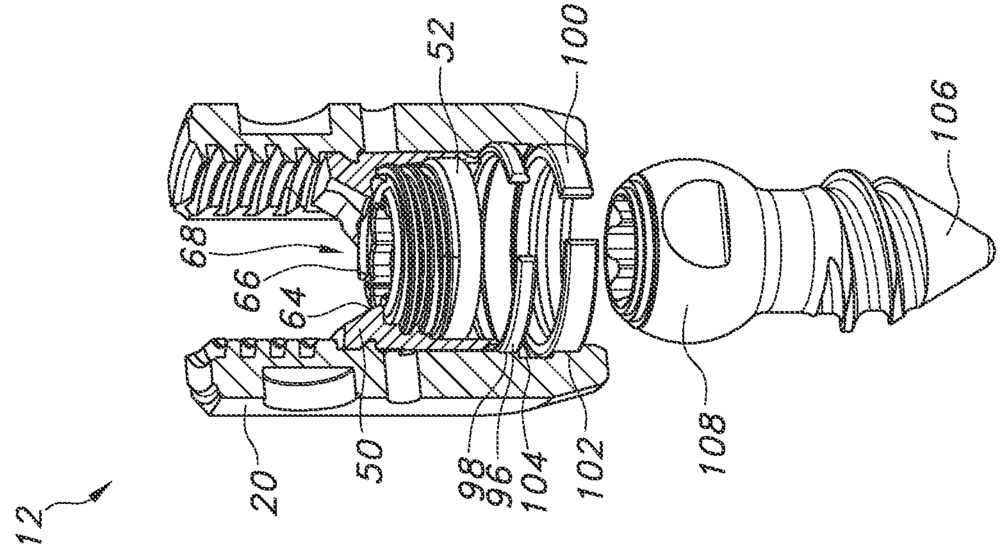
FIG. 7 is a perspective view in part cross section of components of the system shown in FIG. 1 with parts separated.
Figure 11:
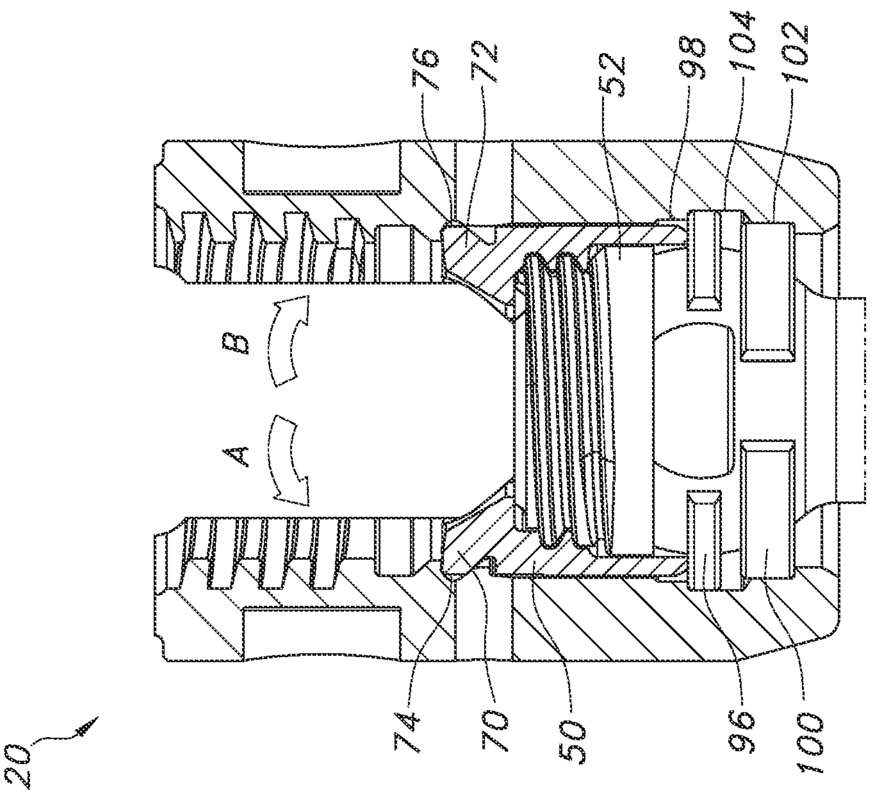
FIG. 11 is a side view of the components of the system shown in FIG. 10.
Figure 10:
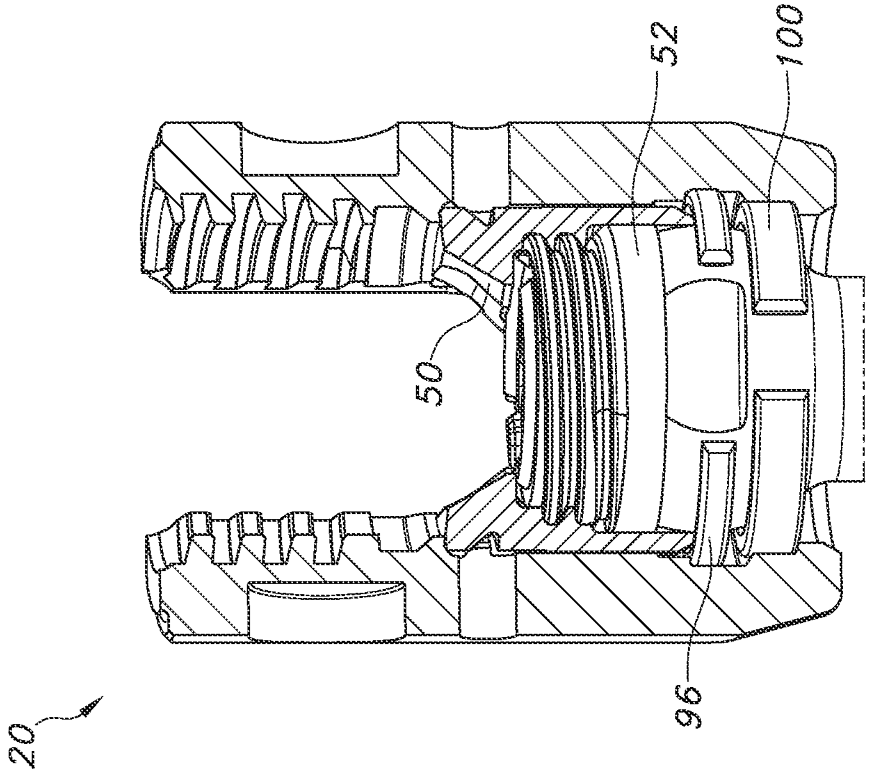
FIG. 10 is a perspective view in part cross section of components shown in FIG. 1.
Figure 13:
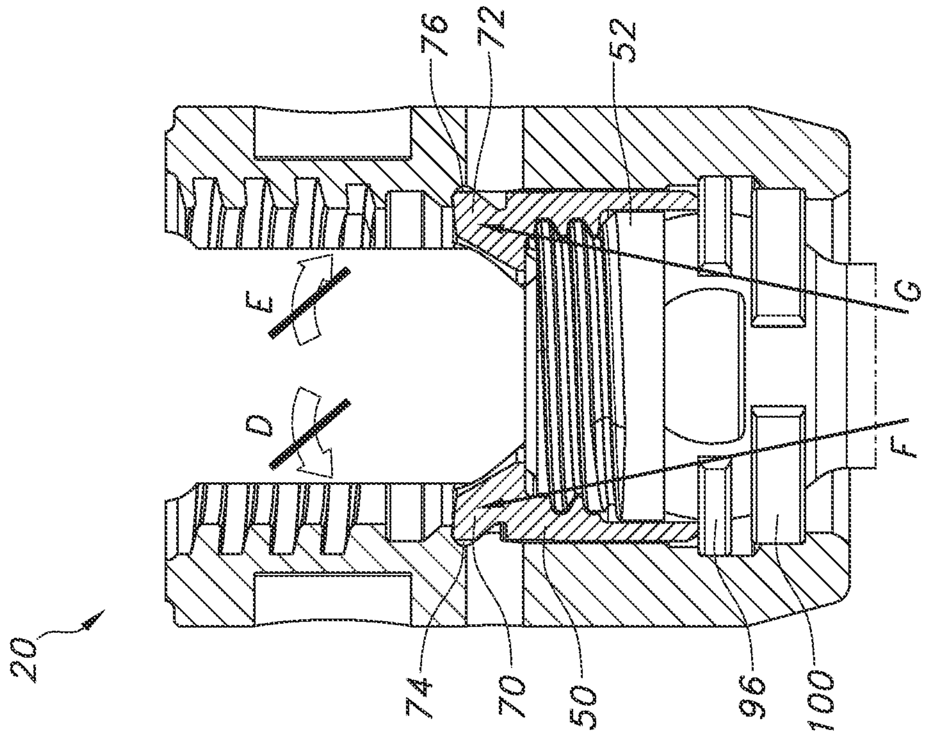
FIG. 13 is a side view of the components shown in FIG. 12.
Figure 12:
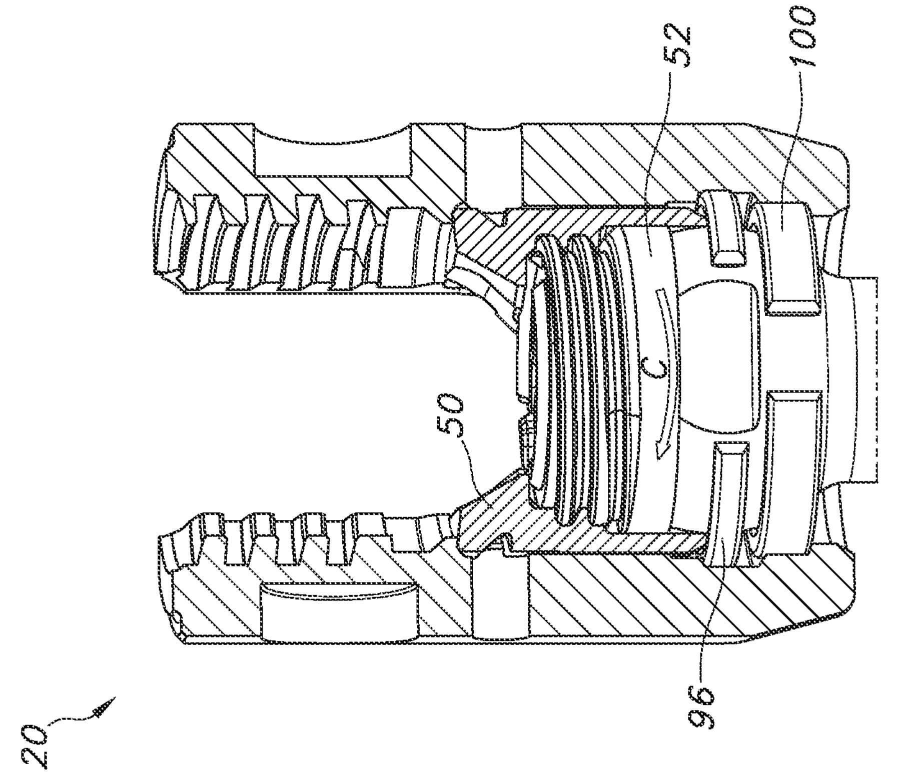
FIG. 12 is a perspective view of components of the system shown in FIG. 10.

Bone fastener 12 includes a crown 50 configured for engagement with receiver 20 and a crown 52 configured for engagement with shaft 106. Crown 52 is movable relative to crown 50 to fix receiver 20 relative to shaft 106 in a selected orientation, as described herein. In some embodiments, crown 50 and/or 52 may be expandable, as shown in FIGS. 7-9, to fix receiver 20 relative to shaft 106 in a selected orientation. For example, crown 52 is movable relative to crown 50 between a non locking orientation/pivoting position, as shown in FIGS. 10 and 11, such that receiver 20 and shaft 106 are relatively movable, and a locking orientation/fixed axial screw position, as shown in FIGS. 12 and 13, such that receiver 20 is fixed relative to shaft 106 in a selected orientation, as described herein. In the non locking orientation, receiver 20 and shaft 106 include multi axial relative movement and in the locking orientation, relative movement between receiver 20 and shaft 106 is fixed.

Figure 4:
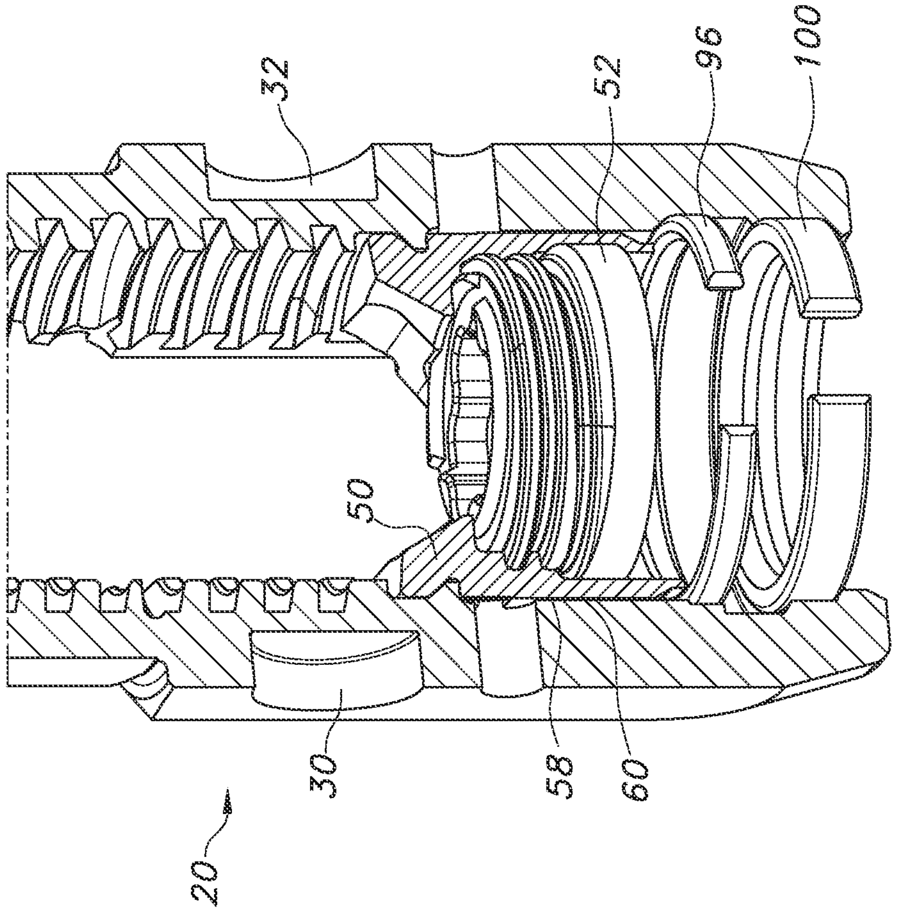
FIG. 4 is a break away view in part cross section of components shown in FIG. 3.
Figure 3:
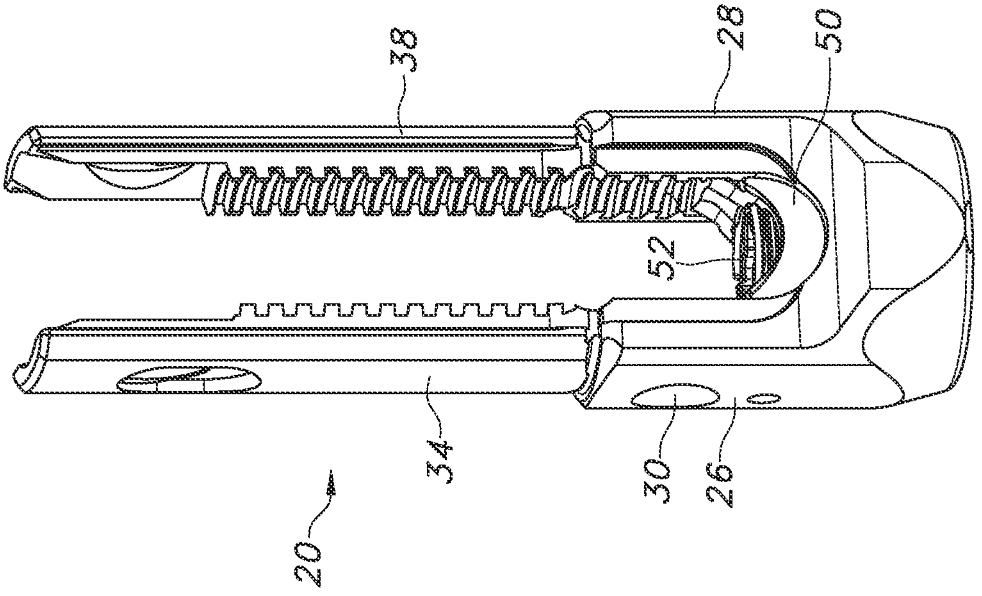
FIG. 3 is a perspective view of components of the system shown in FIG. 1.

Crown 50 is axially translatable relative to crown 52 to fix receiver 20 relative to shaft 106 in a selected orientation. Crown 50 extends between a proximal end 54 and a distal end 56. End 54 includes a proximal circumferential surface 58 engageable with an inner surface 60 of receiver 20, as shown in FIG. 4. In some embodiments, crown 50 includes a gap 62. Gap 62 is configured to facilitate deformation of crown 50 to allow disposal of crown 50 with cavity 46. A proximal surface 64 of crown 50 is disposed with a proximal surface 66 of crown 52 to define an implant receiving surface 68, as shown in FIG. 7. Rod 14 is engageable with implant receiving surface 68 to fix receiver 20 relative to shaft 106 in the selected orientation. In some embodiments, proximal surface 64 may have various surface configurations, for example, smooth, rough, arcuate, undulating, porous, semi-porous, dimpled, polished and/or textured.

Proximal surface 64 of crown 50 includes circumferential flanges 70, 72 configured for engagement with detents 74, 76 of inner surface 60 of receiver 20, as shown in FIGS. 11 and 13. In some embodiments, flanges 70, 72 and/or detents 74, 76 may have various cross section configurations, for example, oval, oblong, triangular, rectangular, square, polygonal, irregular, uniform, non-uniform, variable and/or tapered.

Crown 52 extends between a proximal end 78 and a distal end 80. End 78 includes proximal surface 66 and end 80 includes a distal circumferential surface 82 engageable with a ball, for example, a head 108 of shaft 106. Crown 52 includes a through hole 53. In some embodiments, a surgical tool (not shown) is configured for disposal with through hole 53 such that the surgical tool can disengage shaft 106 from crown 52. Crown 52 includes an outer threaded surface 84 engageable with an inner threaded surface 86 of crown 50. In some embodiments, threaded surfaces 84, 86 may include a single thread turn or a plurality of discrete threads. In some embodiments, an outer surface of crown 52 may alternatively include a set of ratchet teeth (not shown) engageable with a snap ring (not shown). In some embodiments, an outer surface of crown 52 or an inner surface of crown 50 may alternatively include a set of ratchet teeth engageable with positive detents (not shown) of the inner surface of crown 50 or the outer surface of crown 52.

Figure 5:
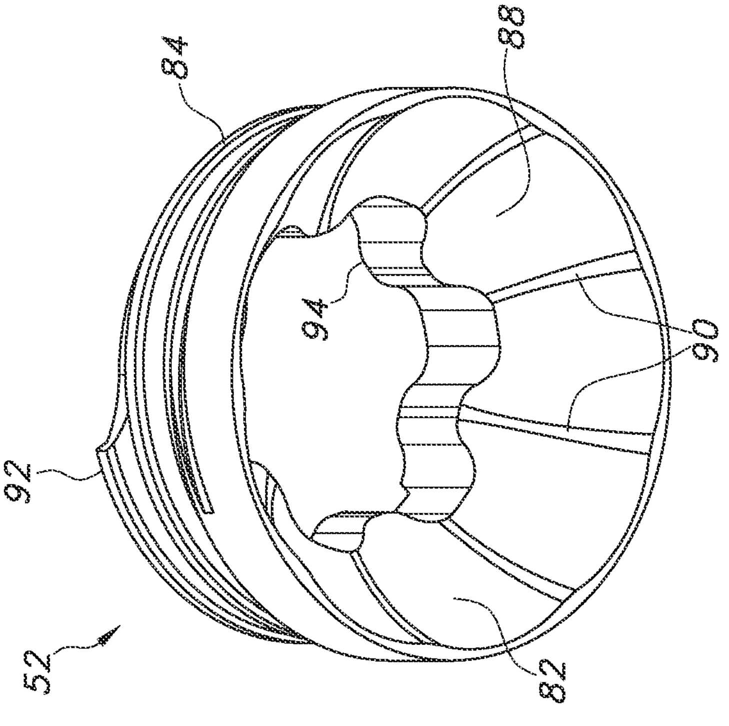
FIG. 5 is a perspective view of a component of the system shown in FIG. 1.

Surface 82 defines an inner socket 88 that includes at least one deformable ridge, for example a plurality of ribs 90, as shown in FIG. 5. Ribs 90 are circumferentially disposed about socket 88. Socket 88 and ribs 90 are configured to engage a ridged surface 109 of head 108 of shaft 106 to prevent movement of receiver 20 around head 108. In some embodiments, ribs 90 are configured to deform against ridged surface 109 of head 108, and displaced material of the deformed ribs 90 is configured to provide additional slip resistance during engagement of socket 88 with head 108 as compared to a crown with a single, smooth socket feature. In some embodiments, ridged surface 109 is large enough to provide additional material for movement resistance as compared to a smooth socket, yet small enough to crush easily during tightening. In some embodiments, all or portions of socket 88 and/or ribs 90 may have various surface configurations, for example, rough, arcuate, undulating, porous, semi-porous, dimpled, and/or textured to enhance fixation between crown 52 and head 108. In some embodiments, ribs 90 are disposed about socket 88 in series, parallel, offset, and/or staggered configurations.

Figure 6:
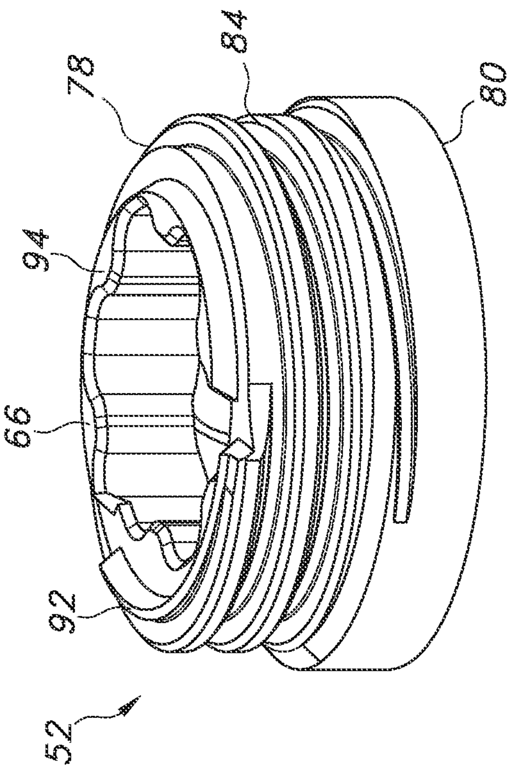
FIG. 6 is a perspective view of the component of the system shown in FIG. 5.

Proximal surface 66 of crown 52 is engageable with flanges 70, 72 of crown 50. Proximal surface 66 includes a deformable raised ridge 92 and a deformable raised ridge 94, as shown in FIGS. 5 and 6. In some embodiments, ridge 92 is configured to increase an amount of thread for engaging crown 50. In some embodiments, ridge 92 increases an amount of thread for engaging crown 50 and ridge 92 crushes to allow rod 14 to fully contact surface 66 of crown 52. Ridge 94 is configured for increasing engagement of a surgical tool, for example, a driver (not shown) with crown 52.

Bone fastener 12 includes a resilient member, for example, a ring 96. Inner surface 60 of receiver 20 defines a circumferential upper groove 98, as shown in FIG. 11, that is configured for disposal of ring 96. Ring 96 is contractable in upper groove 98. Ring 96 includes a circumference that defines an opening, for example, a gap. In some embodiments, the gap is sized such that the gap has a thickness that is less than the height and the width. In some embodiments, the gap is sized to allow ring 96 to translate through cavity 46 by contracting circumferentially. In some embodiments, upon disposal of ring 96 with upper groove 98, surfaces of upper groove 98 resist and/or prevent axial translation of ring 96 relative to longitudinal axis AA.

Bone fastener 12 includes a resilient member, for example, a ring 100. Inner surface 60 of receiver 20 defines a circumferential lower groove 102. Lower groove 102 is configured for disposal of ring 100. Ring 100 includes a circumference that defines an opening, for example, a gap. In some embodiments, the gap is sized such that the gap has a thickness that is less than the height and the width. In some embodiments, the gap is sized to allow ring 100 to translate through cavity 46 by contracting circumferentially. In some embodiments, upon disposal of ring 100 with lower groove 102, surfaces of lower groove 102 resist and/or prevent axial translation of ring 100 relative to longitudinal axis AA. Inner surface 60 defines an expansion groove 104. Ring 100 is expandable in expansion groove 104 to connect receiver 20 and shaft 106.

Rings 96, 100 facilitate manual engagement/connection of receiver 20 and shaft 106. In some embodiments, rings 96, 100 facilitate manual engagement/connection of receiver 20 and shaft 106 such that shaft 106 is attached with receiver 20 in a non-instrumented snap-fit assembly, as described herein.

In some embodiments, manual engagement and/or non-instrumented assembly includes a practitioner, surgeon and/or medical staff grasping shaft 106 and receiver 20 and forcibly snap fitting the components together, as described herein. In some embodiments, manual engagement and/or non-instrumented assembly includes a practitioner, surgeon and/or medical staff grasping shaft 106 and receiver 20 and forcibly pop fitting the components together and/or pop fitting receiver 20 onto shaft 106, as described herein. In some embodiments, a force in a range of 2-50 N is required to manually engage shaft 106 and receiver 20 and forcibly assemble the components. For example, a force in a range of 2-50 N is required to snap fit and/or pop fit assemble shaft 106 and receiver 20. In some embodiments, a force in a range of 5-10 N is required to manually engage shaft 106 and receiver 20 and forcibly assemble the components. For example, a force in a range of 5-10 N is required to snap fit and/or pop fit assemble shaft 106 and receiver 20. In some embodiments, shaft 106 is manually engaged with receiver 20 in a non-instrumented assembly, as described herein, such that removal of receiver 20 and shaft 106 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

Shaft 106 includes a threaded portion 110 engageable with tissue, for example, vertebral tissue. In some embodiments, threaded portion 110 may include a single thread turn or a plurality of discrete threads. Head 108 includes a tool engaging portion 112 configured to engage a surgical tool or instrument, as described herein. In some embodiments, portion 112 includes a hexagonal cross-section. In some embodiments, head 108 includes an outer surface having planar surfaces or flats and/or arcuate surfaces.

In a non locking/pivoting orientation, as shown in FIGS. 10 and 11, socket 88 of crown 52 facilitates pivoting receiver

Figure 15:
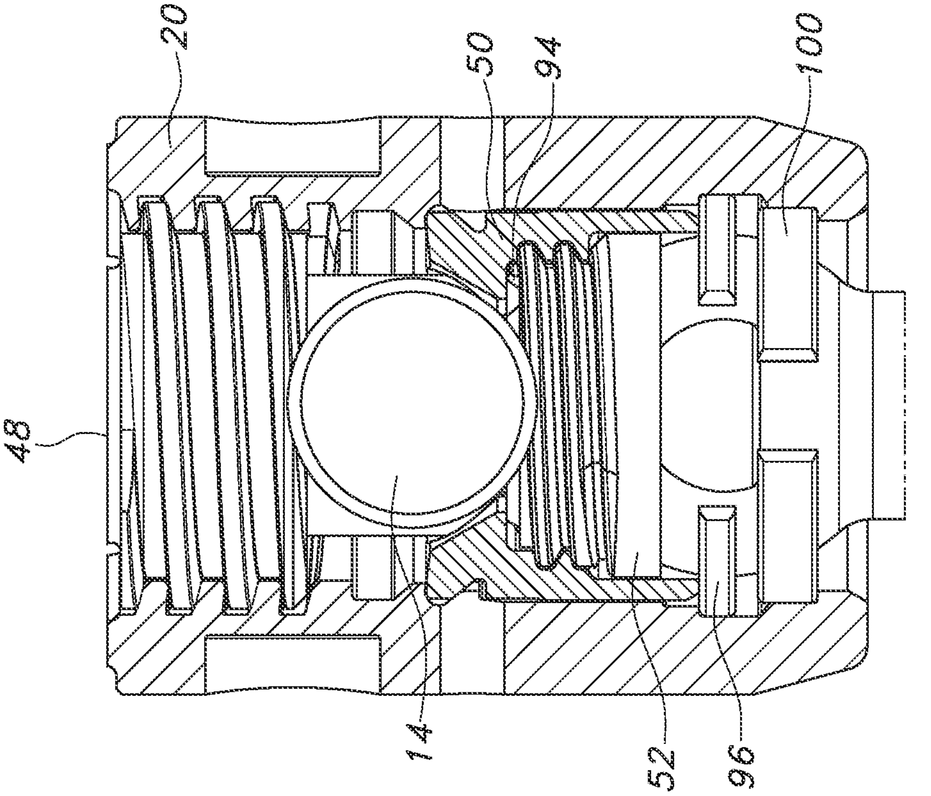
FIG. 15 is a side view of the components of the system shown in FIG. 14.
Figure 14:
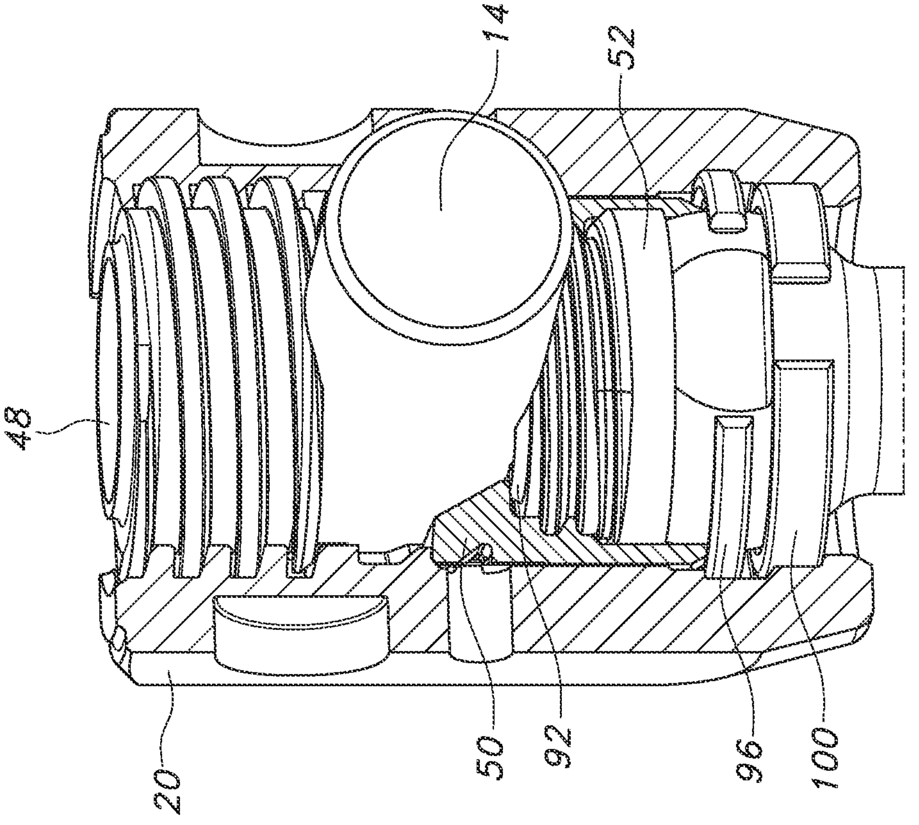
FIG. 14 is a perspective view in part cross section of components of the system shown in FIG. 1.
Figure 17:
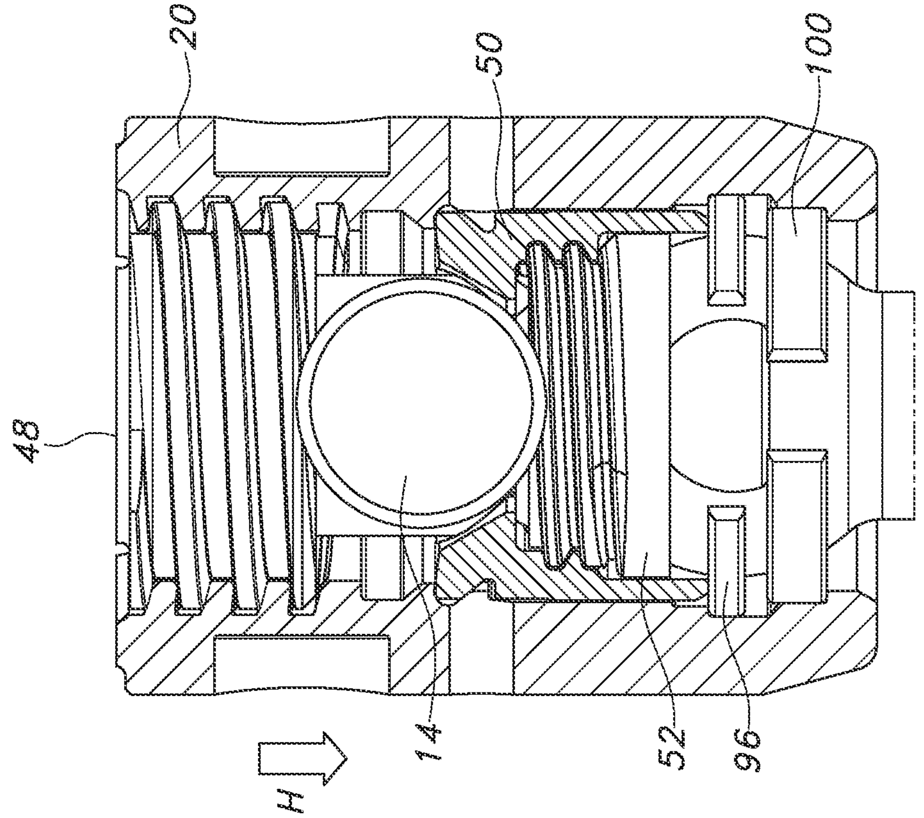
FIG. 17 is a side view in part cross section of the components of the system shown in FIG. 16.
Figure 16:
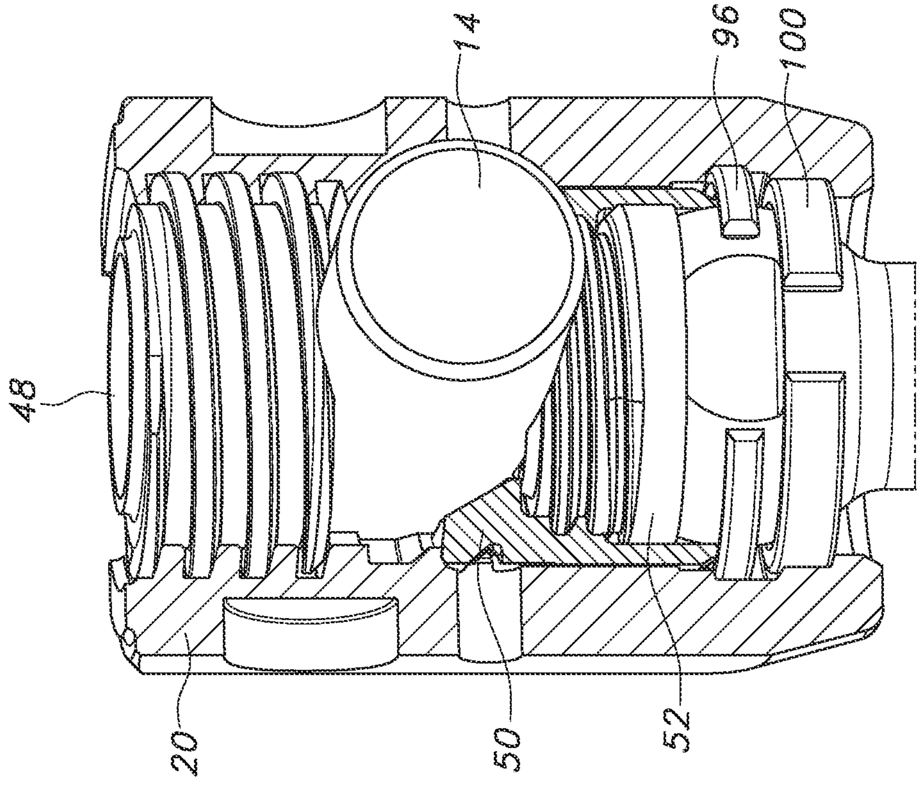
FIG. 16 is a side view in part cross section of components of the system shown in FIG. 1.

20 relative to head 108 of shaft 106, in selected directions, as shown by arrows A and B in FIG. 11. In a locking orientation/fixed axial screw position, crown 52 is threaded within crown 50, in a direction, for example, a clockwise direction, as shown by arrow C in FIG. 12 and socket 88 via ribs 90 of crown 52 engages surface 109 of shaft 106 to prevent movement, for example, pivoting of receiver 20 relative to head 108 of shaft in directions shown by arrows D and E in FIG. 13. Ribs 90 provide an increased grip on head 108 to prevent movement of receiver 20. Crown 50 via flanges 70, 72 is translated to engage detents 74, 76 to create an opposing force of crown 52, as shown by arrows F and G in FIG. 13. In the locked orientation, rod 14 is fixed with receiver 20. Rod 14 is fixed to bone fastener 12 via setscrew 48, as shown in FIGS. 14-15. Setscrew 48 engages with receiver 20 and rod 14, and is tightened.

As shown in FIGS. 14-15, ridges 92, 94 are thin enough to be crushed by rod 14 such that rod 14 directly engages with surface 66 of crown 52, ensuring a stable connection between rod 14 and crown 52. Engagement between crown 52 and rod 14 for an extended period of time ensures that as setscrew 48 is tightened, receiver 20 is forcibly oriented perpendicular relative to rod 14. In some embodiments, in the locking orientation/fixed axial screw position, as setscrew 48 is tightened, bone fastener 12 is oriented perpendicular to rod 14, and vertebra of a patient can be moved when shaft 106 is anchored into the vertebra.

In some embodiments, bone fastener 12 is configured for disposal in a multi axial orientation. In some embodiments, this configuration maintains maneuverability and the ability of receiver 20 to pivot, for example, during rod 14 insertion. In some embodiments, the multi axial orientation can be locked after rod 14 is inserted into receiver 20 and set screw 48 is tightened. In some embodiments, set screw 48 is translated, as shown by arrow H in FIG. 17, toward rod 14, driving socket 88 of crown 52 onto surface 109 of shaft 106 to prevent pivoting of receiver 20. In some embodiments, this configuration maintains relative pivotable movement of receiver 20 during rod 14 insertion such that receiver 20 can be variably positioned and/or facilitate ease of rod 14 disposal.

In assembly, operation and use, spinal implant system 10, similar to the systems and methods described herein, includes a bone fastener 12 having receiver 20 connectable with a shaft 106, as described herein, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, spinal implant system 10 comprises a spinal implant kit, which includes one or more selected receivers 20, as described herein, which are configured for connection with one or more interchangeable shafts 106 to facilitate disposal of bone fasteners 12 along vertebrae of a patient, as described herein. In some embodiments, the one or more selected interchangeable shafts 106 interface with selected interchangeable receivers 20 to comprise one or more bone fasteners 12 and/or configurations. The components of bone fasteners 12 and one or a plurality of spinal implants, for example, rod 14 can be delivered or implanted as a pre-assembled device or can be assembled in situ. In some embodiments receiver 20 can be assembled with shaft 106 on a back table of an operating room and inserted into a vertebra pre-assembled. The components of spinal implant system 10 may be completely or partially revised, removed or replaced.

In use, to treat a selected section of vertebrae, including vertebra V, a medical practitioner obtains access to a surgical site including vertebrae in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae, as well as for aspiration and irrigation of a surgical region.

One or more shafts 106 are fixed with vertebra V, as shown in FIGS. 18-21, such that shaft 106 is manipulated to drive, torque, insert and/or align shaft 106 with vertebra V along a selected trajectory. Receiver 20 is disposed with shaft 106 in a snap-fit assembly, as shown in FIGS. 7-9 and described herein. Receiver 20 is assembled with each shaft 106 by translating receiver, in a direction shown by arrow I in FIG. 8. Engagement of head 108 of shaft 106 with cavity 46 causes a surface of head 108 to engage with ring 100 such that ring 100 is translated, in a direction shown by arrow J in FIG. 8, disposing ring 100 into expansion groove 104 in an expanded orientation. Head 108 translates further through cavity 46 in the direction shown by arrow J and passes further through ring 100 as ring 100 is driven back into lower groove 102. Ring 100 resiliently contracts into its natural state around head 108.

Crowns 50, 52 are manipulated, for example, via engagement by a surgical driver or inserter (not shown), to translate crown 52, in a direction, for example, a downward direction, as shown by arrow K in FIG. 9, to engage receiver 20 with head 108 and crown 50 via flanges 70, 72 is translated below detents 74, 76. End 80 of crown 52 engages ring 96 to dispose ring 96 into expansion groove 104 such that ring 96 resiliently opens into its natural orientation. Ring 96 is oriented for abutting and/or contacting engagement with ring 100 to resist and/or prevent translation of ring 100 from lower groove 102 into expansion groove 104, and thus providing connection of the components of bone fastener 14 including capture of head 108 of shaft 106.

Figure 19:
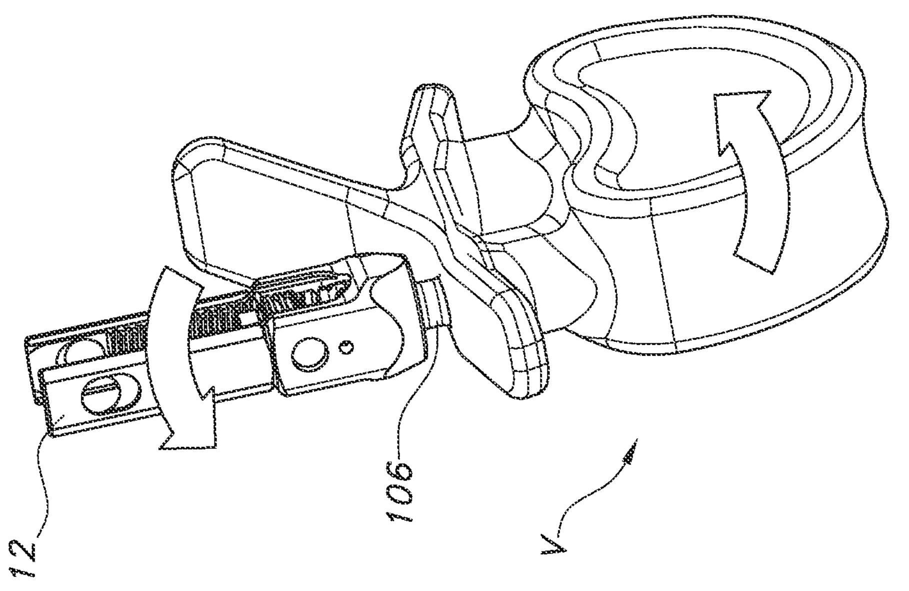
FIG. 19 is a perspective view of components of one embodiment of a spinal implant system in accordance with the principles of the present disclosure disposed with vertebra.
Figure 18:
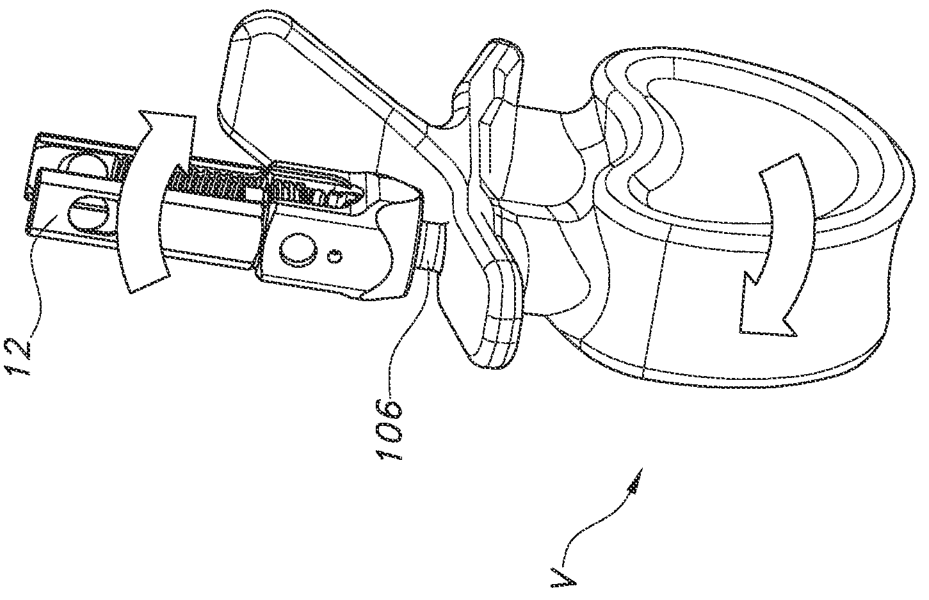
FIG. 18 is a perspective view of components of one embodiment of a spinal implant system in accordance with the principles of the present disclosure disposed with vertebra.
Figure 21:
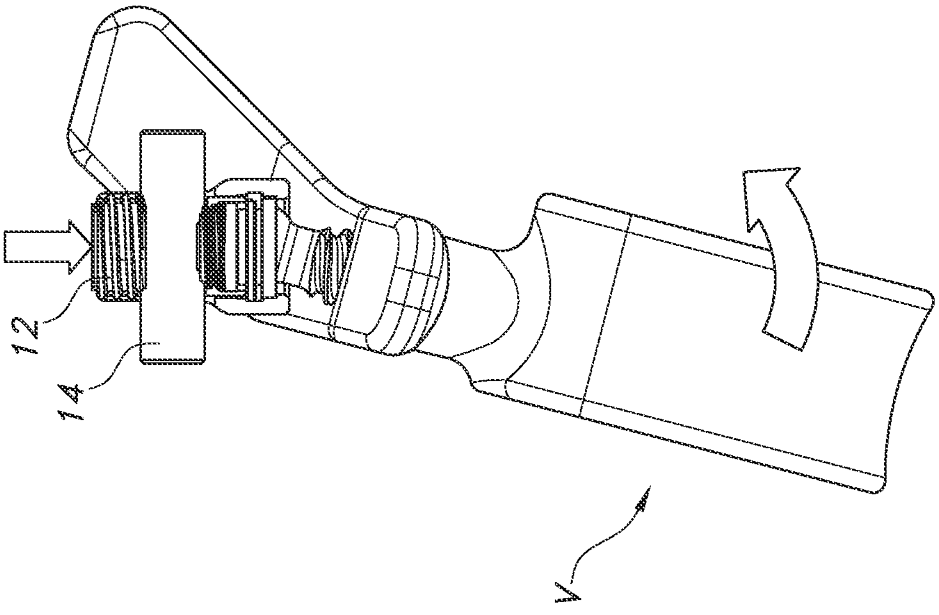
FIG. 21 is a perspective view of components of one embodiment of a spinal implant system in accordance with the principles of the present disclosure disposed with vertebra.
Figure 20:
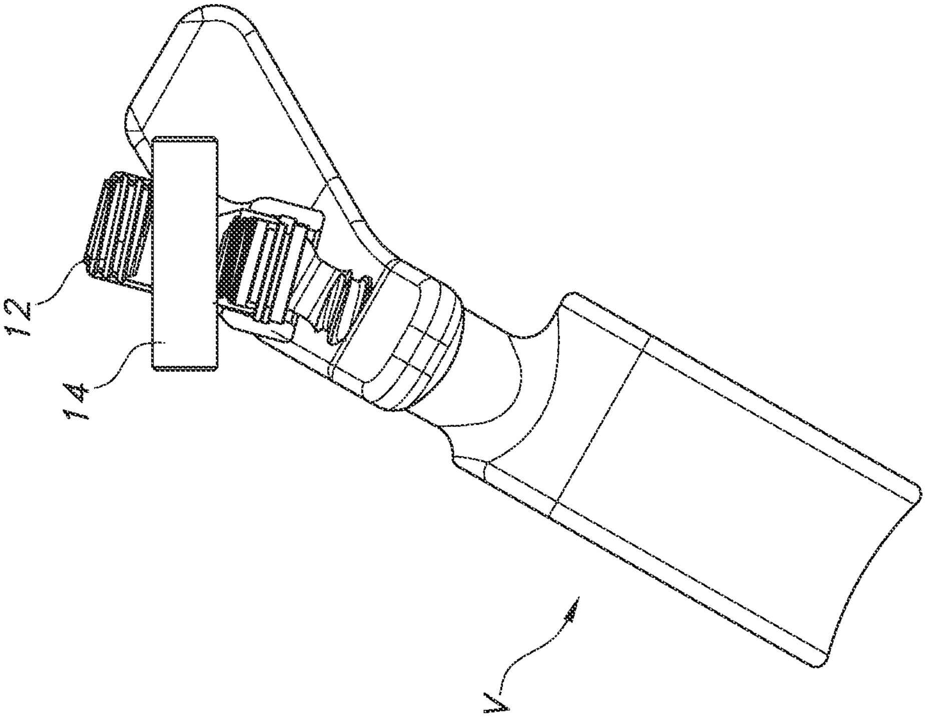
FIG. 20 is a perspective view of components of one embodiment of a spinal implant system in accordance with the principles of the present disclosure disposed with vertebra.
Figure 22:
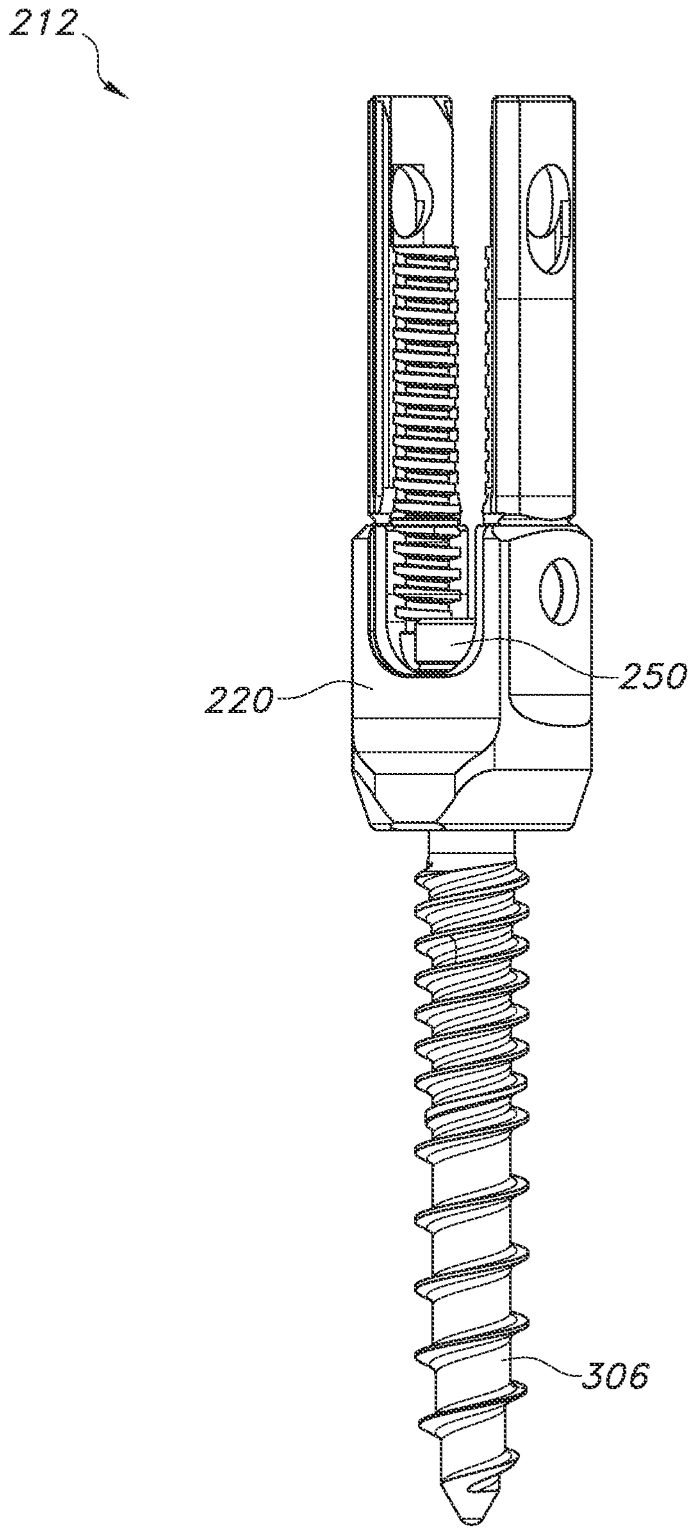
FIG. 22 is a perspective view of components of one embodiment of a spinal implant system in accordance with the principles of the present disclosure.
Figure 23:
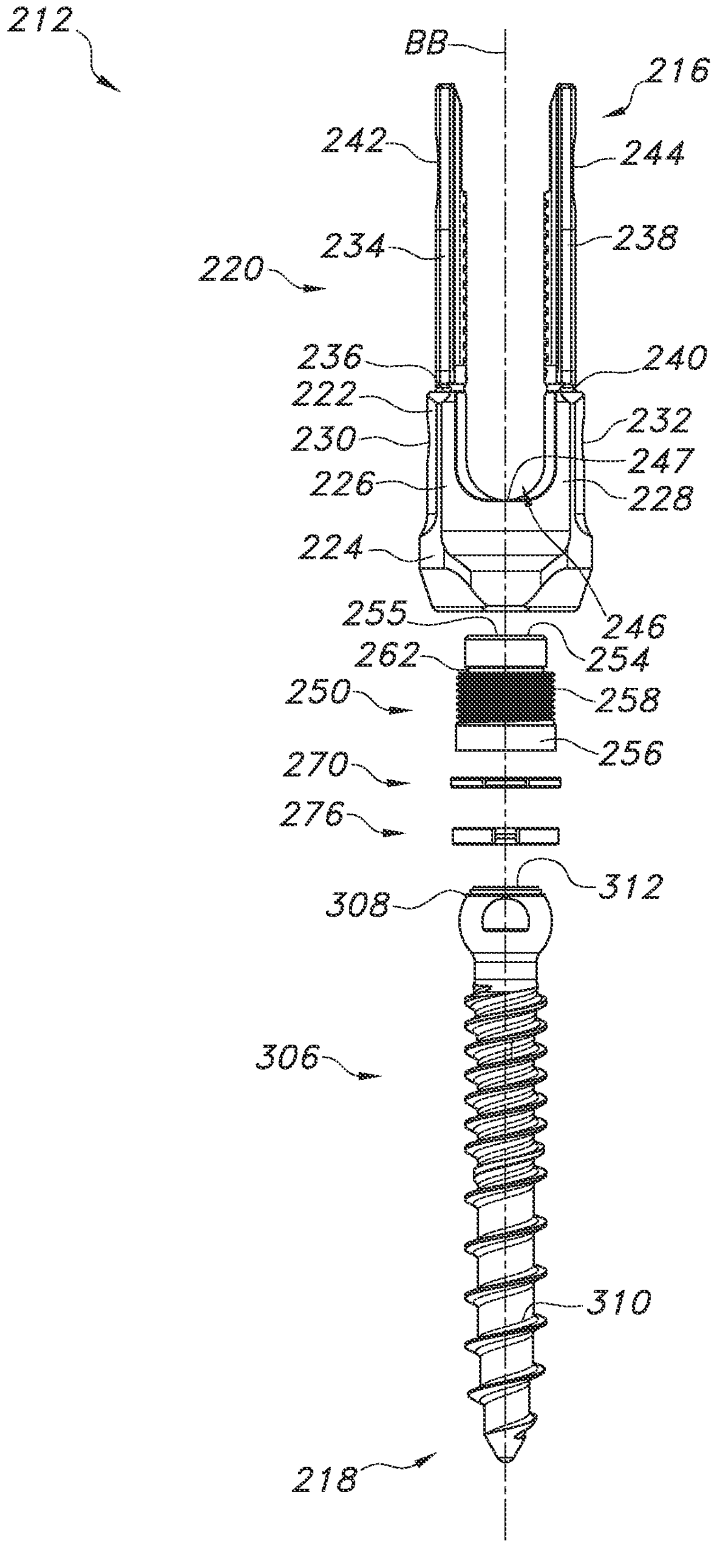
FIG. 23 is a perspective view of the components of the system shown in FIG. 22 with parts separated.
Figure 24:
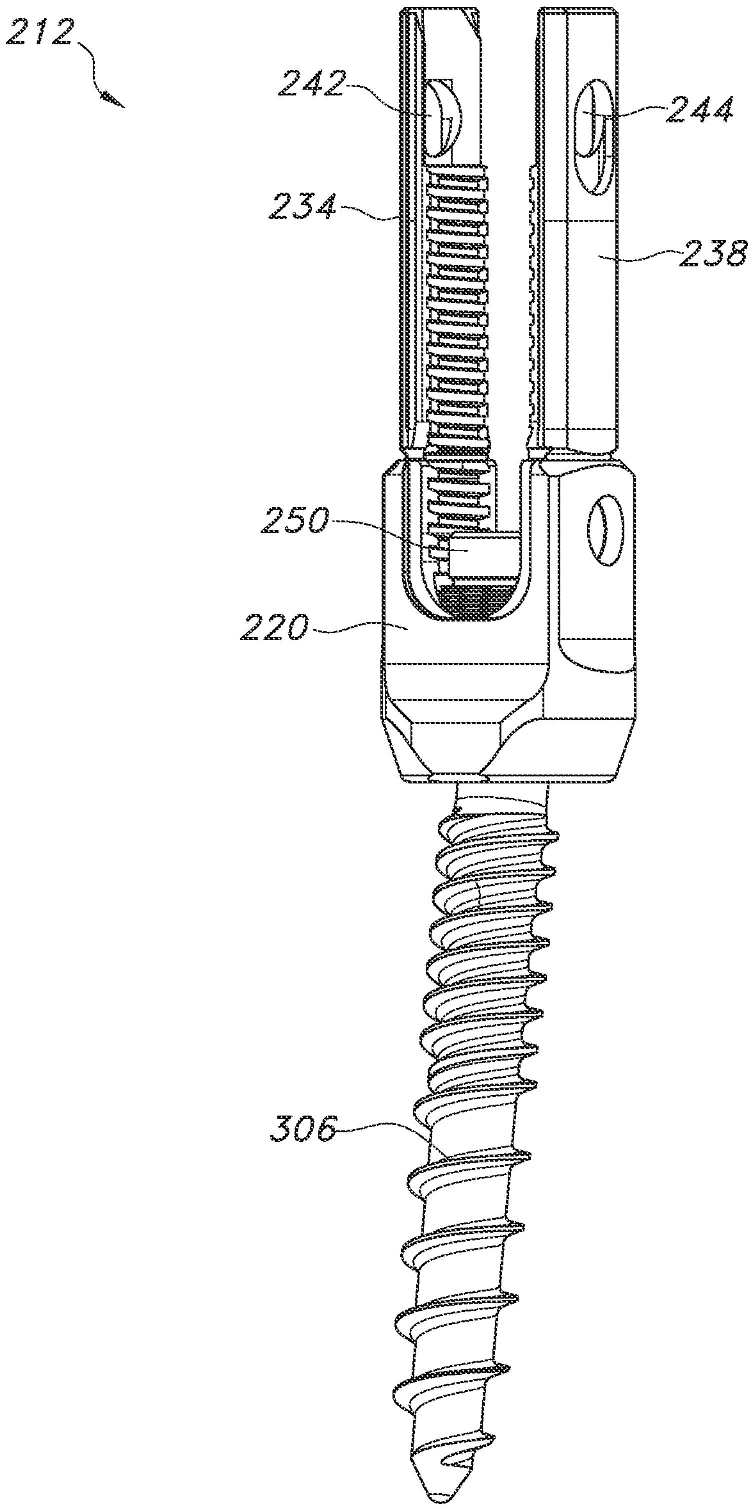
FIG. 24 is a perspective view of the components of the system shown in FIG. 22.

In a non locking orientation, socket 88 of crown 52 facilitates selectively pivoting of receiver 20 relative to head 108 of shaft 106, for example, in the directions shown by arrows A and B in FIG. 11. In the locking orientation/fixed axial screw position, crown 52 is threaded within crown 50, in the clockwise direction, as shown by arrow C in FIG. 12 and socket 88 via ribs 90 of crown 52 engages surface 109 of shaft 106 to fix the components and prevent movement of receiver 20 relative to head 108, for example, as shown by arrows D and E in FIG. 13. Ribs 90 provide a grip and/or frictional engagement on head 108 to prevent movement of receiver 20. Crown 50 via flanges 70, 72 is translated to engage detents 74, 76 to create an opposing force of crown 52, as shown by arrows F and G in FIG. 13. In the locked orientation, rod 14 is fixed with receiver 20. Rod 14 is fixed to bone fastener 12 via setscrew 48, as shown in FIGS. 14 and 15. Setscrew 48 engages with receiver 20 and rod 14, and is tightened. In some embodiments, bone fastener 12 is fixed with selected vertebra V, as shown in FIGS. 18-19, such that bone fastener 12 can manipulate vertebra V, as shown in FIGS. 20-21, using receiver 20 as receiver 20 is locked in a fixed angle orientation in connection with a surgical procedure, for example, a correction procedure. In some embodiments, as set screw 48 is tightened, bone fastener 12 and therefore vertebra V are oriented to rod 14, to correct the spine.

In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, one or more bone fasteners, as described herein, may be engaged with tissue in various orientations, for example, series, parallel, offset, staggered and/or alternate vertebral levels. In some embodiments, the bone fasteners may comprise multi-axial screws, sagittal adjusting screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 22-30, spinal implant system 10, similar to the systems and methods described herein, includes a bone fastener 212, similar to bone fastener 12. Bone fastener 212 is configured for fixation with a surgical site including vertebral tissue via a member, for example, a shaft 306. Bone fastener 212 includes a member, for example, a receiver 220 configured to receive a spinal implant, for example, a spinal rod 14. Receiver 220 is movable to a selected orientation relative to vertebral tissue and fixable in the selected orientation, as described herein. In some embodiments, bone fastener 212 includes a multi-axial bone screw such that receiver 220 is movable to a selected orientation relative to vertebral tissue and is fixable in the selected orientation, as described herein. In some embodiments, bone fastener 212 is disposable in a selected orientation via selective angulation of receiver 220, as described herein. In some embodiments, bone fastener 212 includes a fixed-multi axial screw. In some embodiments, bone fastener 212 is configured to de-rotate vertebral tissue without fully fixating rod 14 with receiver 220, described herein. Bone fastener 212 extends between an end 216, an end 218 and defines a longitudinal axis BB.

Receiver 220 is movable relative to shaft 306. Receiver 220 extends between a proximal end 222 and a distal end 224. End 222 includes an arm 226 and an arm 228, similar to arms 26, 28 described herein. In some embodiments, arms 226, 228 each extend parallel to axis BB. Arm 226 is configured for connection with an extension 234, similar to extension 34 described herein, via a break away surface 236 and arm 228 is configured for connection with an extension 238, similar to extension 38 described herein, via a break away surface 240. Break away surfaces 236, 240 are configured to fracture and separate at a predetermined force or torque limit, similar to that described herein. Receiver 220 defines an implant cavity 246, similar to implant cavity 46 described herein. Receiver 220 includes a rod slot, for example, an implant receiving surface 247. Rod 14 is configured to be seated within implant receiving surface 247 and is configured for engagement with a setscrew (not shown) to fix rod 14 with bone fastener 212.

Figure 25:
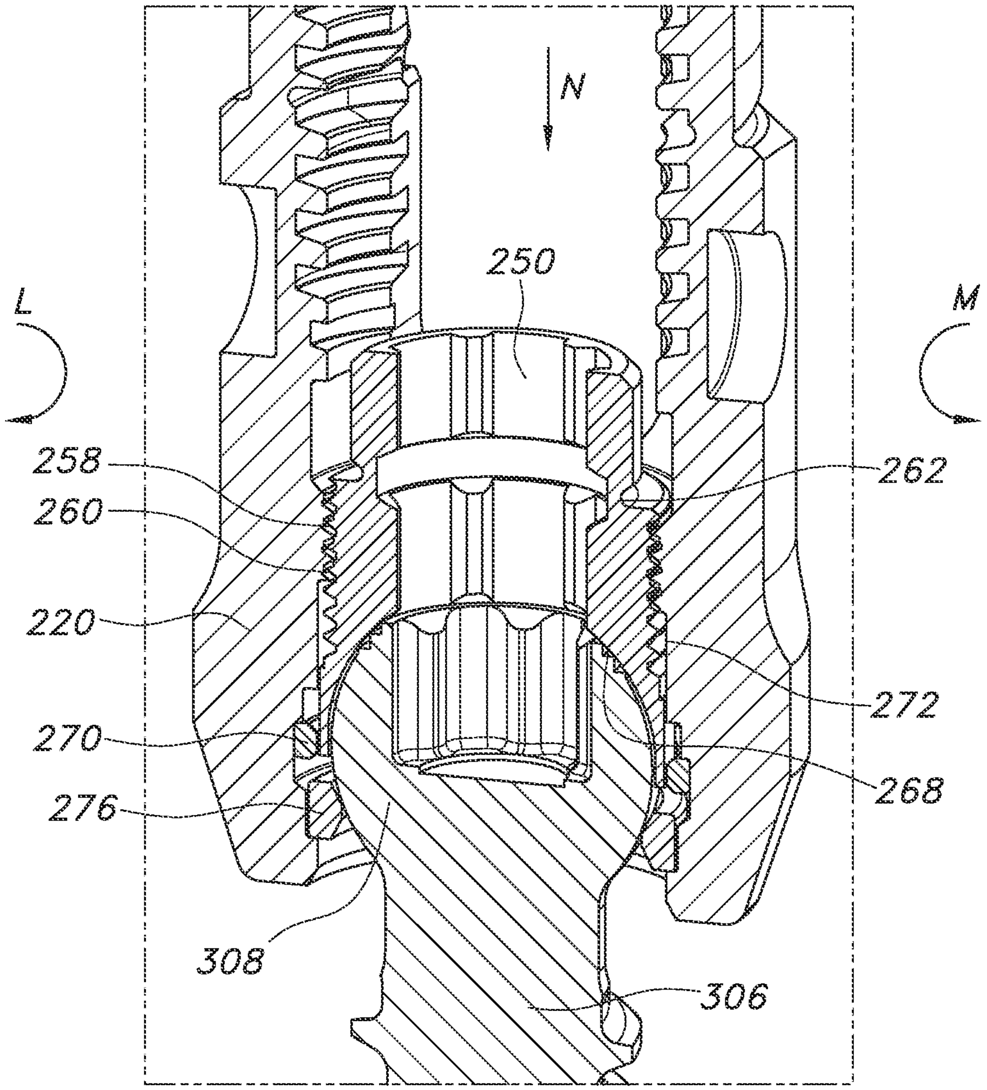
FIG. 25 is a break away cross section view of components of the system shown in FIG. 22.

Bone fastener 212 includes a crown 250 configured for engagement with receiver 220 and shaft 306 to fix receiver 220 relative to shaft 306 in a selected orientation, as described herein. Crown 250 extends between a proximal portion, for example, a setscrew portion 254 and a distal portion 256. Crown 250 includes a through hole 255. In some embodiments, a surgical tool (not shown) is configured for disposal with through hole 255 such that the surgical tool can disengage shaft 306 from crown 250. Crown 250 includes an outer threaded surface 258 configured for engagement with an inner threaded surface 260 disposed at distal end 224 of receiver 220, as shown in FIG. 25. In some embodiments, threaded portions 258, 260 may include a single thread turn or a plurality of discrete threads.

Figure 27:
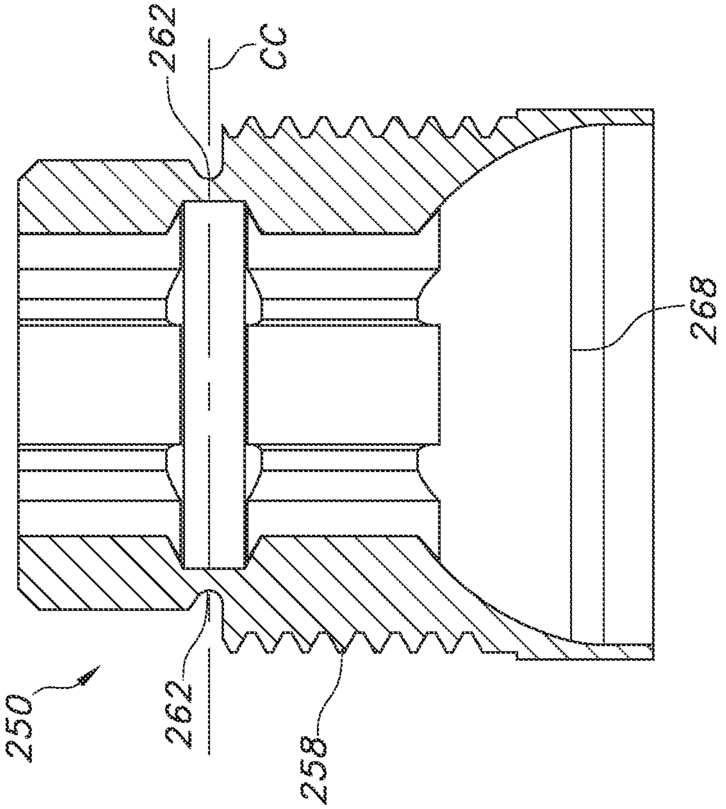
FIG. 27 is a cross section view of the component of the system shown in FIG. 26.
Figure 26:
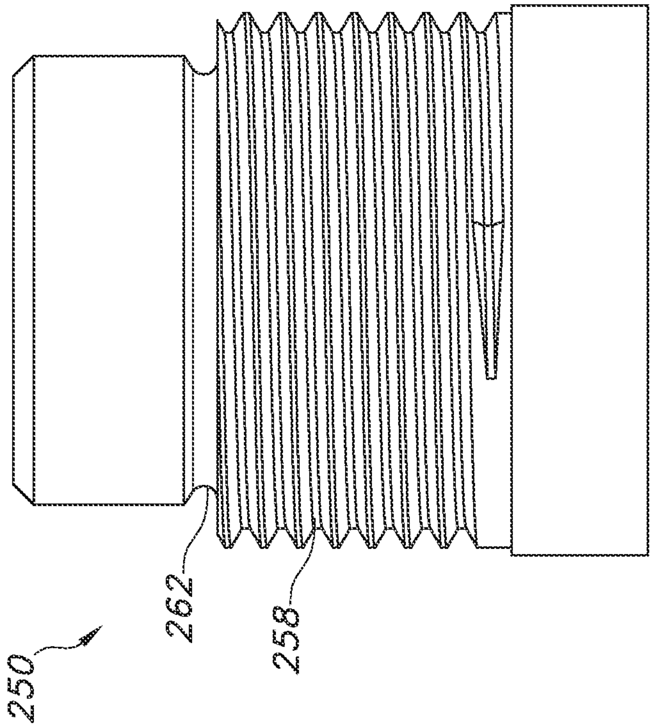
FIG. 26 is a side view of a component of the system shown in FIG. 22.

Crown 250 includes a break away surface 262, as shown in FIGS. 25 and 27. Break away surface 262 is configured to connect portions 254, 256, and portion 254 is removable from the portion 256 via break away surface 262 to fix and lock receiver 220 in a selected orientation. Break away surface 262 is disposed on a longitudinal axis CC that is transverse relative to axis BB, as shown in FIG. 27. Break away surface 262 is configured to fracture and separate at a predetermined force or torque limit, as described herein. In some embodiments, break away surface 262 is fabricated from a fracturing and/or frangible material such that manipulation of break away surface 262 can fracture and separate portion 254 from portion 256 at a predetermined force and/or torque limit, described herein. Break away surface 262 has a reduced thickness relative to portions 254, 256 to facilitate fracture and separation. In the depicted embodiment, portion 254 is illustrated as extending a short distance above break away surface 262 but may extend further, such as beyond arms 226, 228.

In some embodiments, break away surface 262 includes a predetermined force or torque limit including a range of approximately 2 to 12 Nm. In some embodiments, portions 254, 256 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 254, 256. In some embodiments, crown 250 may not include a break away surface, and a torque limiting instrument (not shown) is implemented to apply a selected amount of tightening torque to crown 250.

Figure 30:
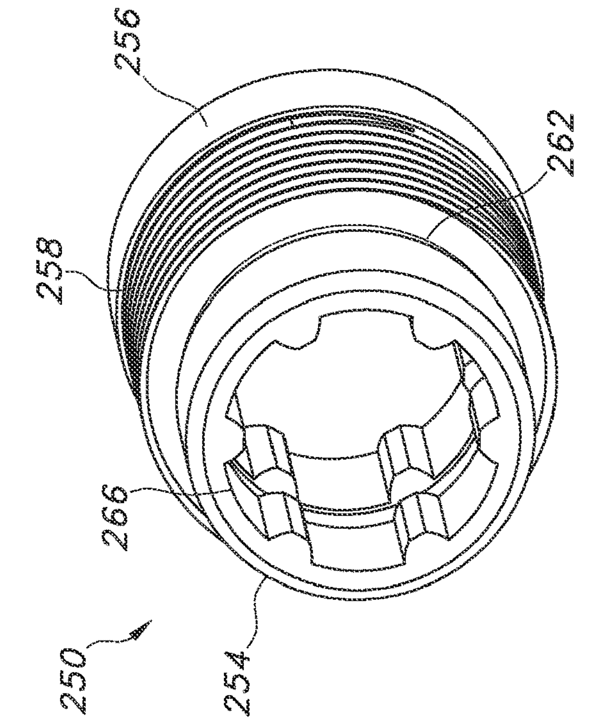
FIG. 30 is a perspective view of the component of the system shown in FIG. 26.
Figure 29:
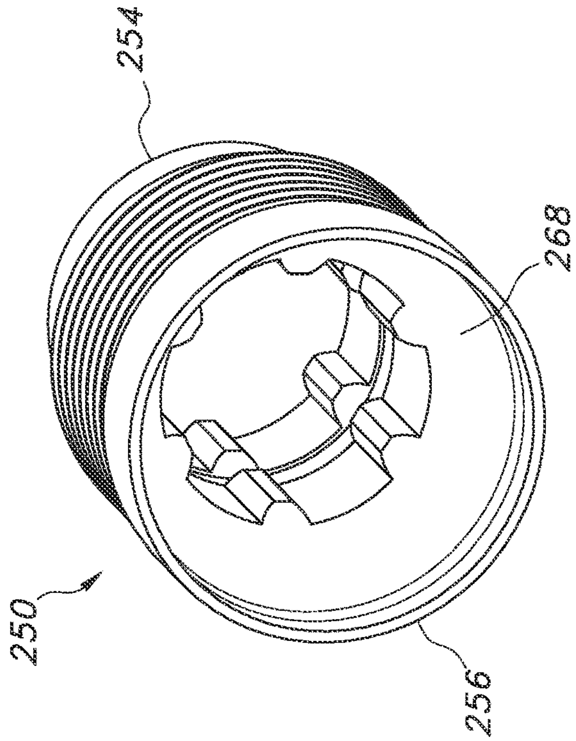
FIG. 29 is a perspective view of the component of the system shown in FIG. 26.
Figure 28:
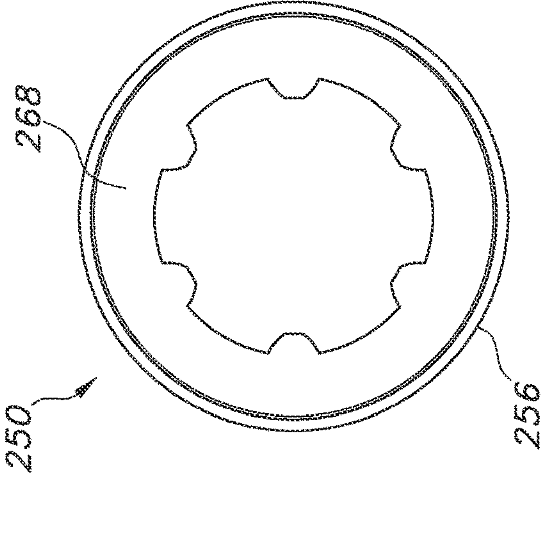
FIG. 28 is a bottom view of the component of the system shown in FIG. 26.

Portion 254 defines a tool engaging portion 266 configured to engage a surgical tool or instrument, as shown in FIG. 30. In some embodiments, portion 266 includes a hexagonal cross-section. Portion 256 defines an inner socket 268, as shown in FIGS. 27-29, configured to engage a head 308 of shaft 306, as shown in FIG. 25. In some embodiments, all or portions of socket 268 may have various surface configurations, for example, rough, arcuate, undulating, porous, semi-porous, dimpled, and/or textured to enhance engagement between crown 250 and head 308. In some embodiments, socket 268 may include ridges similar to ridges 90, described herein.

Bone fastener 212 includes rings 270, 276 that facilitate manual engagement/connection of receiver 220 and shaft 306, similar to that described herein. In some embodiments, rings 270, 276 facilitate manual engagement/connection of receiver 220 and shaft 306 such that shaft 306 is attached with receiver 220 in a non-instrumented snap-fit assembly, as described herein.

Shaft 306 includes a threaded portion 310 engageable with tissue, for example, vertebral tissue. In some embodiments, threaded portion 310 may include a single thread turn or a plurality of discrete threads. Head 308 includes a tool engaging portion 312 configured to engage a surgical tool or instrument, as described herein. In some embodiments, portion 312 includes a hexagonal cross-section. In some embodiments, head 308 includes an outer surface having planar surfaces or flats and/or arcuate surfaces.

In assembly, operation and use, spinal implant system 10 includes bone fastener 212 having receiver 220 connectable with shaft 306, as described herein, and is employed with a surgical procedure for treatment of a spinal disorder affecting a section of a spine of a patient, as discussed herein. In use, for example, receiver 220 is disposed with shaft 306 in a snap-fit assembly, similar to that described herein. Receiver 220 is rotatable in a selected orientation, for example, directions shown by arrows L and M in FIG. 25. Crown 250 via threaded surface 258 threadingly engages with threaded surface 260 of receiver 220 and is translated in a direction, shown by arrow N in FIG. 25 via a break off driver (not shown). Portion 254 of crown 250 is removed via break away surface 262 at a selected predetermined force or torque limit to fix bone fastener 212 in a selected fixed angle screw configuration. In some embodiments, rod 14 is fixed to receiver 220 via a setscrew (not shown).

In some embodiments, bone fastener 212 includes a modular fixed-multi axial screw that provides alignment of one or more receivers 220 prior to translating rod 14 through receivers 220 and maintains receivers 220 in a selected orientation. In some embodiments, bone fastener 212 includes a modular fixed-multi axial screw that facilitates de-rotation maneuvers before rod 14 is fixed with the bone fasteners 212.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:

a first member defining an implant cavity;

a second member movable relative to the first member and penetrable with tissue;

a first crown engageable with the first member; and a second crown engageable with the second member, the second crown being movable relative to the first crown to fix the first member relative to the second member in a selected orientation;

wherein the second crown includes an outer threaded surface engageable with an inner threaded surface of the first crown;

wherein the second crown includes a distal surface engageable with a head of the second member, the distal surface comprising a plurality of deformable ribs circumferentially disposed about an approximate center of the second crown; and wherein each one of the plurality of deformable ribs is disposed in a spaced apart relation to one another and extend radially outward between an interior perimeter and an exterior perimeter of the second crown.

2. A spinal implant as recited in claim 1, wherein the second crown is movable relative to the first crown between a non locking orientation such that the members are relatively movable and a locking orientation such that the first member is fixed relative to the second member in the selected orientation.

3. A spinal implant as recited in claim 2, wherein in the non locking orientation the members include multi axial relative movement.

4. A spinal implant as recited in claim 1, wherein the first crown includes a proximal circumferential surface engageable with an inner surface of the first member and the second crown includes a distal circumferential surface engageable with a head of the second member.

5. A spinal implant as recited in claim 1, wherein a proximal surface of the first crown is disposed with a proximal surface of the second crown to define an implant receiving surface.

6. A spinal implant as recited in claim 5, further comprising a spinal rod engageable with the implant receiving surface to fix the first member relative to the second member in the selected orientation.

7. A spinal implant as recited in claim 1, wherein the first crown is axially translatable relative to the second crown to fix the first member relative to the second member in the selected orientation.

8. A spinal implant as recited in claim 1, wherein the first member defines one or more grooves; and further comprising one or more bands configured for disposal within the one or more grooves and engageable with a head of the second member to connect the members such that the first member is movable relative to the second member.

9. A spinal implant as recited in claim 1, wherein the first member includes a receiver having a first arm connected to a first extension and a second arm connected to a second extension, the arms being connected to the extensions via a break away surface.

10. A spinal implant comprising:

a receiver defining an implant cavity and one or more grooves;

a shaft movable relative to the receiver;

one or more bands configured for disposal within the one or more grooves and engageable with a head of the shaft to connect the receiver and the shaft such that the receiver is movable relative to the shaft;

a first crown engageable with the receiver; and a second crown engageable with the shaft and movable relative to the first crown between a non locking orientation such that the receiver and the shaft include multi axial relative movement and a locking orientation such that the receiver is fixed relative to the shaft in a selected orientation;

wherein the second crown includes an outer threaded surface engageable with an inner threaded surface of the first crown;

wherein the second crown includes an inner socket and a distal surface engageable with a head of the shaft, the distal surface including a plurality of deformable ribs circumferentially disposed on the inner socket about an approximate center of the second crown;

wherein each one of the plurality of deformable ribs is disposed in a spaced apart relation to one another and extends radially outward between an interior perimeter and an exterior perimeter of the second crown; and wherein a proximal end of a flange defines a proximal end of the first crown.

11. A spinal implant as recited in claim 10, wherein a proximal surface of the first crown is disposed with a proximal surface of the second crown to define an implant receiving surface, and further comprising a spinal rod engageable with the implant receiving surface to fix the shaft relative to the receiver in the selected orientation.

* * * * *